US006861239B1

(12) United States Patent  
Blumenberg et al.

(10) Patent No.: US 6,861,239 B1  
(45) Date of Patent: Mar. 1, 2005

(54) GENES AND POLYNUCLEOTIDES ASSOCIATED WITH ULTRAVIOLET RADIATION-MEDIATED SKIN DAMAGE AND USES THEREOF

(75) Inventors: Miroslav Blumenberg, New York, NY (US); Alix M. Gazel, Leucate (FR)

(73) Assignee: New York University, New York, NY (US)

( * ) Notice: Subject to any disclaimer, the term of this patent is extended or adjusted under 35 U.S.C. 154(b) by 35 days.

(21) Appl. No.: 09/659,737

(22) Filed: Sep. 11, 2000

Related U.S. Application Data

(60) Provisional application No. 60/155,029, filed on Sep. 20, 1999.

(51) Int. Cl.[7] .............................. C12N 9/12; C12N 1/20; C12N 15/00; C12N 5/00; C07H 21/04
(52) U.S. Cl. .......................... 435/194; 435/6; 435/325; 435/320.1; 435/252.3; 536/23.2
(58) Field of Search ........................... 435/194, 6, 325, 435/320.1, 252.3; 536/23.2

(56) References Cited

U.S. PATENT DOCUMENTS 5,854,043 A   12/1998   Johnson ...................... 435/194

FOREIGN PATENT DOCUMENTS

CA          2 369 172       10/1999

OTHER PUBLICATIONS

Diener et al., "Activation of the c–Jun N–terminal Kinase Pathway by a Novel Protein Kinase Related to Human Germinal Center Kinase," Proc. Natl. Acad. Sci., USA, vol. 94, 1997, pp 9687–9692.
Tibbles et al., "The Stress–Activated Protein Kinase Pathways," Cellular and Molecular Life Sciences, vol. 55, 1999, pp 1230–1254.
Latkowski et al., "Epidermal Cell Kinetics, Epidermal Differentiation, and Keratinization," Fitzpatrick's Dermatology in Medicine (book) 1999 McGraw Hill pp 133–144.
Herrlich et al., "The Mammalian UV Response: Mechanism of DNA Damage Induced Gene Expression," Advan. Enzyme Regul. vol. 34, 1995, 381–395.
Ullrich et al., "The Role of Cytokines in UV–Induced Systemic Immune Suppression," Journal of Dermatological Science, vol. 23, 2000 Abstract, 510–512.

Ouhtit et al., "Temporal Events in Skin Injury and the Early Adaptive Responses in Ultraviolet–Irradiated Mouse Skin," American Journal of Pathology, vol. 156, No. 1, Jan. 2000, pp 201–207.
Beissert et al., "Mechanisms Involved in Ultraviolet Light–Induced Immunosuppression," J. Investig. Dermatol. Symp. Proc., vol. 4, No. 1, pp 61–63.
Barnes et al., "Mechanisms of Disease," The New England Journal of Medicine, vol. 336, No. 15, Apr. 10, 1997, pp 1066–1071.
Osada et al., "YSK1, a novel mammalian protein kinase structurally related to Ste 20 and SPS1, but is not involved in the known MAPK pathways" Oncogene vol. 14, 1997, pp 2047–2057.
Dorow et al., "Identification of a new family of human epithelial protein kinases containing two leucine/isoleucine–zipper domains," Eur. J. Biochem., vol. 213, No. 2, 1993, 701–710.
Su et al., "Signal transduction by the JNK MAPK cascade and ultraviolet light induced cytokine gene expression," Photochemistry and Photobiology, vol. 67, Special Issue, 1998, 60S.
Abo et al., "PAK4, a Novel Effector for Cdc42Ha, is Implicated in the Reorganization of the Actin Cytoskeleton and in the Formation of Filopodia," EMBO Journal, vol. 17, pp 6527–6540, 1998.
Broun et al., "Catalytic Plasticity of Fatty Acid Modification Enzymes Underlying Chemical Diversity of Plant Lipids," Science, vol. 282, Nov. 13, 1998, pp 1315–1317.
Ng et al., "Point Mutation in the Second Phosphatase Domain of CD45 Abrogates Tyrosine Phosphatase Activity," Biochemcial and Biophysical Research Communications, vol. 206, No. 1, Jan. 5, 1995, pp 302–309.

*Primary Examiner*—Maryam Monshipouri
(74) *Attorney, Agent, or Firm*—Wilmer Cutler Pickering Hale and Dorr LLP

(57) ABSTRACT

The invention relates to novel polynucleotides and their encoded gene products that are expressed in skin cells, particularly keratinocytes, and methods of using the same. Specifically, the present invention provides polynucleotides encoding several novel protein kinases that are c-Jun N-terminal kinase kinase kinases, i.e., MLK4, PAK4, PAK5 and YSK2. In addition, the invention provides methods of using the disclosed polynucleotides and their gene products in drug discovery, particularly in screening for drugs that can reduce ultraviolet light-induced damage of the skin, inflammation and psoriasis, and drugs that can enhance wound healing.

12 Claims, 3 Drawing Sheets

Figure 1:
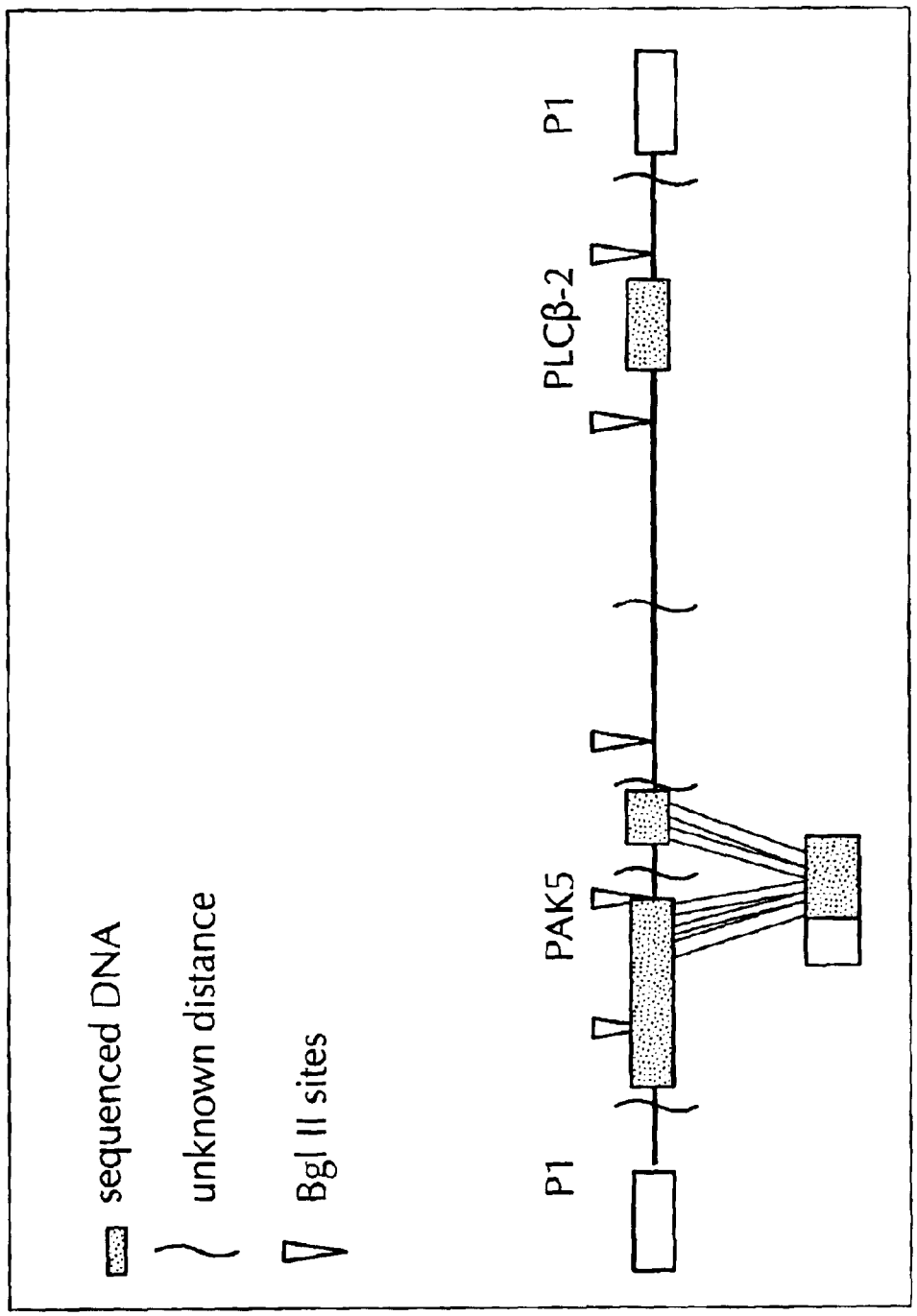

Northern blot 10 mJ/cm² 1 hr post illumination

Differential Display.

Note strong induction of Pak5, but not of Pak4, by UVA light.

GENES AND POLYNUCLEOTIDES ASSOCIATED WITH ULTRAVIOLET RADIATION-MEDIATED SKIN DAMAGE AND USES THEREOF

This application claims priority from provisional application Ser. No. 60/155,029, filed Sep. 20, 1999, which is incorporated herein by reference in its entirety.

1. FIELD OF THE INVENTION

The invention provides novel polynucleotides, and their encoded gene products, that are expressed in skin cells, particularly keratinocytes, and methods of using the same. Specifically, the present invention relates to novel protein kinases that are c-Jun N-terminal kinase kinase kinases (JNKKKs). In addition, the invention provides methods of using the novel polynucleotides and their encoded products in drug discovery, particularly in screening for drugs that can reduce ultraviolet light-induced damage of the skin, inflammation and psoriasis, and drugs that can enhance wound healing.

2. BACKGROUND OF THE INVENTION

Many extracellular signals, such as light, growth factors, cytokines and chemical or physical stresses, activate multi-tiered kinase cascades in the cytoplasm of cells. For example, a growth factor such as epidermal growth factor (EGF) will bind to its cognate receptor on the cell surface, thereby activating the intercellular protein ras, which is associated with the cytoplasmic portion of the cell surface receptor. Ras phosphorylates and thereby activates raf1, a mitogen-activated protein kinase kinase kinase (MAPKKK). Raf1 then induces (also by phosphorylation) the activation of mitogen-activated protein kinase kinases (MEKs), which in turn phosphorylate extracellular signal regulated kinases (ERKs). When phosphorylated, ERKs translocate to the nucleus where they phosphorylate and thus activate transcription factors such as stress activated protein kinase 1 (SAP1) and ternary complex factor Elk1. See, e.g., Fanger et al., 1997, Current Opin. Genet. Dev. 7:67–74.

Stress (such as heat and ultraviolet (UV) light) and cytokines (such as TNF- and IL-1) activate their own sets of kinase-kinase-kinases, termed JNKKKs. These, in turn, act on specific JNKKs, which activate c-Jun-N terminal kinase (JNK) and p38. The last two kinases enter the nucleus, where they phosphorylate and activate transcription factors. See, e.g., Diene et al., 1997, PNAS 94:9687–92.

Most of the initial events in the cellular responses to different stresses have not been elucidated so far. However, it is clear that different extracellular signals activate different members of the JNKKK family. Thus, some JNKKKs are specifically responsive to TNF-α, others to osmotic shock, yet others to UV illumination. Diene et al., 1997, above; Raingeaud et al., 1995, J. Biol. Chem. 270:7420–6.

Skin cells such as keratinocytes are particularly susceptible to ultraviolet radiation damage. However, very little is known about how keratinocytes respond to ultraviolet radiation stress. Manipulation of keratinocyte responses to environmental stress could result in therapies for a wide variety of skin disorders, as well as cosmetic uses.

Therefore, there is a great need in the art to elucidate the components involved in keratinocyte signal transduction that can be used as targets for drug screening. Accordingly, this invention provides several novel JNKKKs expressed by keratinocytes and involved in the cellular response to ultraviolet radiation, and uses thereof.

3. SUMMARY OF THE INVENTION

The present invention relates to polynucleotide molecules having nucleotide sequences that encode portions of several novel JNKKK gene products including an MLK4 kinase, a PAK4 kinase, a PAK5 kinase, and a YSK2 kinase, as well as the amino acid sequences encoded by these polynucleotide sequences. The present invention further relates to polynucleotide molecules having nucleotide sequences that encode a PAK5 kinase.

In one aspect, the invention provides an isolated polynucleotide molecule comprising a nucleotide sequence encoding a portion of a human MLK4 gene product. In a preferred embodiment, the portion of the MLK4 gene product comprises the amino acid sequence of SEQ ID NO:2. In a non-limiting embodiment, the isolated polynucleotide molecule of the present invention comprises the nucleotide sequence of SEQ ID NO:1.

The present invention further provides an isolated polynucleotide molecule that is homologous to a polynucleotide molecule comprising the nucleotide sequence of SEQ ID NO:1. The present invention further provides an isolated polynucleotide molecule comprising a nucleotide sequence that encodes a polypeptide having an amino acid sequence that is homologous to the amino acid sequence of SEQ ID NO:2.

The present invention further provides an isolated polynucleotide molecule consisting of a nucleotide sequence that is a substantial portion of any of the aforementioned MLK4-related polynucleotide molecules of the present invention. In a preferred embodiment, the substantial portion of the MLK4-related polynucleotide molecule consists of a nucleotide sequence that encodes a peptide fragment of a human MLK4 gene product or MLK4-related homologous polypeptide of the present invention. In a specific though non-limiting embodiment, the present invention provides a polynucleotide molecule consisting of a nucleotide sequence encoding a peptide fragment consisting of a sub-sequence of the amino acid sequence of SEQ ID NO:2.

In another aspect, the invention provides an isolated polynucleotide molecule comprising a nucleotide sequence encoding a portion of a human PAK4 gene. In a preferred embodiment, the portion of the PAK4 gene product comprises the amino acid sequence of SEQ ID NO:4. In a non-limiting embodiment, the isolated polynucleotide molecule of the present invention comprises the nucleotide sequence of SEQ ID NO:3.

The present invention further provides an isolated polynucleotide molecule that is homologous to a polynucleotide molecule comprising the nucleotide sequence of SEQ ID NO:3. The present invention further provides an isolated polynucleotide molecule comprising a nucleotide sequence that encodes a polypeptide having an amino acid sequence that is homologous to the amino acid sequence of SEQ ID NO:4.

The present invention further provides an isolated polynucleotide molecule consisting of a nucleotide sequence that is a substantial portion of any of the aforementioned PAK4-related polynucleotide molecules of the present invention. In a preferred embodiment, the substantial portion of the PAK4-related polynucleotde molecule consists of a nucleotide sequence that encodes a peptide fragment of a human PAK4 gene product or PAK4-related homologous polypeptide of the present invention. In a specific though non-limiting embodiment, the present invention provides a polynucleotide molecule consisting of a nucleotide sequence encoding a peptide fragment consisting of a subsequence of the amino acid sequence of SEQ ID NO:4.

In another aspect, the invention provides an isolated polynucleotide molecule comprising a nucleotide sequence encoding a portion of a human PAK5 gene product. In a preferred embodiment, the portion of the PAK5 gene product comprises the amino acid sequence of SEQ ID NO:6. In a non-limiting embodiment, the isolated polynucleotide molecule encoding the amino acid sequence of SEQ ID NO:6 comprises the nucleotide sequence of SEQ ID NO:5.

In another aspect, invention provides an isolated polynucleotide molecule comprising a portion of the nucleotide sequence of the human PAK5 gene, which portion encodes a polypeptide comprising the amino acid sequence of SEQ ID NO:8. In a non-limiting embodiment, the isolated polynucleotide molecule encoding the amino acid sequence of SEQ ID NO:8 comprises the nucleotide sequence of SEQ ID NO:7.

The present invention further provides an isolated polynucleotide molecule that is homologous to a polynucleotide molecule comprising the nucleotide sequence of SEQ ID NO:5 or SEQ ID NO:7. The present invention further provides an isolated polynucleotide molecule comprising a nucleotide sequence that encodes a polypeptide having an amino acid sequence that is homologous to the amino acid sequence of SEQ ID NO:6 or SEQ ID NO:8.

In another aspect, the invention provides an isolated polynucleotide molecule comprising a nucleotide sequence encoding the complete human PAK5 gene product having the amino acid sequence of SEQ ID NO:10. In a preferred embodiment, the polynucleotide molecule comprises the nucleotide sequence of SEQ ID NO:9 from nt 199 to nt 2244, which represents the ORF of the cDNA. In another non-limiting embodiment, the isolated polynucleotide molecule encoding the complete human PAK5 gene product comprises the nucleotide sequence of the ORF of SEQ ID NO:11 from nt 6125 to nt 17,433.

The present invention further provides an isolated polynucleotide molecule that is homologous to a polynucleotide molecule comprising the nucleotide sequence of SEQ ID NO:9 or SEQ ID NO:11.

The present invention further provides an isolated polynucleotide molecule consisting of a nucleotide sequence that is a substantial portion of any of the aforementioned PAK5-related polynucleotide molecules of the present invention. In a preferred embodiment, the substantial portion of the PAK5-related polynucleotide molecule consists of a nucleotide sequence that encodes a peptide fragment of a human PAK5 gene product or PAK5-related homologous polypeptide of the present invention.

In another aspect, the invention provides an isolated polynucleotide molecule comprising a nucleotide sequence encoding a portion of a human YSK2 gene product. In a preferred embodiment, the portion of the YSK2 gene product comprises the amino acid sequence of SEQ ID NO:13. In a non-limiting embodiment, the isolated polynucleotide molecule of the present invention comprises the nucleotide sequence of SEQ ID NO:12.

The present invention further provides an isolated polynucleotide molecule that is homologous to a polynucleotide molecule comprising the nucleotide sequence of SEQ ID NO:12. The present invention further provides an isolated polynucleotide molecule comprising a nucleotide sequence that encodes a polypeptide having an amino acid sequence that is homologous to the amino acid sequence of SEQ ID NO:13.

The present invention further provides an isolated polynucleotide molecule consisting of a nucleotide sequence that is a substantial portion of any of the aforementioned YSK2-related polynucleotide molecules of the present invention. In a preferred embodiment, the substantial portion of the YSK2-related polynucleotide molecule consists of a nucleotide sequence that encodes a peptide fragment of a human YSK2 gene product or YSK2-related homologous polypeptide of the present invention. In a specific though non-limiting embodiment, the present invention provides a polynucleotide molecule consisting of a nucleotide sequence encoding a peptide fragment consisting of a sub-sequence of the amino acid sequence of SEQ ID NO:13.

The present invention further provides compositions and methods for cloning and expressing any of the polynucleotide molecules of the present invention, including cloning vectors and expression vectors comprising any of the polynucleotide molecules of the present invention, as well as transformed host cells and novel strains or cell lines derived therefrom comprising any of the polynucleotide molecules, cloning vectors or expression vectors of the present invention. In a non-limiting embodiment, the present invention provides a recombinant expression vector comprising a polynucleotide molecule of the present invention in operative association with one or more regulatory elements for expression of the polynucleotide molecule.

Also provided by the present invention is a substantially purified or isolated polypeptide encoded by a polynucleotide molecule of the present invention. In a specific though non-limiting embodiment, the polypeptide is a portion of a human MLK4 gene product comprising the amino acid sequence of SEQ ID NO:2. In another specific though non-limiting embodiment, the polypeptide is a portion of a human PAK4 gene product comprising the amino acid sequence of SEQ ID NO:4. In another specific though non-limiting embodiment, the polypeptide is a portion of a human PAK5 gene product, comprising the amino acid sequence of either SEQ ID NO:6 or SEQ ID NO:8, or is the entire human PAK5 gene product comprising the amino acid sequence of SEQ ID NO:10 in another specific though non-limiting embodiment, the polypeptide is a portion of a YSK2 gene product, comprising the amino acid sequence of SEQ ID NO:13.

The present invention also provides substantially purified or isolated polypeptides that are homologous to the portions of the human MLK4, PAK 4, PAK5 and YSK2 gene products of the present invention. The present invention also provides a substantially purified or isolated polypeptide that is homologous to the complete human PAK5 gene product of the present invention. The present invention further provides substantially purified or isolated peptide fragments of the MLK4, PAK4, and PAK5 gene products of the present invention, and substantially purified or isolated peptide fragments of the YSK2 gene product of the present invention that have the first six amino acids of SEQ ID NO:13.

The present invention also provides a method of preparing a substantially purified or isolated portion of a human MLK4, PAK4, PAK5 or YSK2 gene product, or a substantially purified or isolated human PAK5 gene product, or a homologous peptide, or peptide fragment of the present invention, comprising culturing host cells transformed with a polynucleotide molecule or vector of the present invention under conditions conducive to the expression therefrom of the polypeptide or peptide fragment of the invention, and recovering the polypeptide or peptide fragment in substantially purified or isolated form from the cell culture.

Also provided are antibodies specific for the MLK4, PAK4, PAK5 or YSK2 gene product, homologous peptide, or peptide fragment of the present invention, and methods of detecting the MLK4, PAK4, PAK5 or YSK2 gene product, homologous peptide, or peptide fragment of the present invention in a sample. Still another aspect of the invention provides methods of identifying compounds that bind to the MLK4, PAK4, PAK5 or YSK2 gene product, homologous peptide, or peptide fragment of the present invention.

The present invention also provides methods of detecting an MLK4, PAK4, PAK5 or YSK2-related polynucleotide in a sample, comprising contacting the sample with a compound that binds to and forms a complex with the particular polynucleotide for a period of time sufficient to form the complex, and detecting the complex, so that if a complex is detected, the MLK4, PAK4, PAK5 or YSK2-related polynucleotide, respectively, is detected. In a non-limiting embodiment, the method comprises contacting the sample under stringent hybridization conditions with nucleic acid primers that anneal to the particular polynucleotide under such hybridization conditions, and amplifying the annealed polynucleotides, so that if a particular polynucleotide is amplified, the MLK4, PAK4, PAK5 or YSK2-related polynucleotide, respectively, is detected.

The invention further provides a method of screening for compounds that affect the cellular levels of a JNKKK gene product, comprising: (a) applying a test compound to a test sample; (b) determining the cellular levels of at least one gene product in the test sample, wherein the gene product is from a gene comprising a nucleotide sequence selected from the group consisting of SEQ ID NOS: 1, 3, 5, 7, 9, 11 and 12; and (c) comparing the levels of the gene product in the test sample with that in a reference sample; wherein a specific change in the cellular levels of the gene product in the test sample as compared to the reference sample indicates that the test compound affects the cellular levels of gene product from a JNKKK gene. In a preferred embodiment, the method further comprises the step of applying a stress event to the test sample and determining the effect of the test compound on the response of the test sample to the stress event.

The invention further provides a method of screening for compounds that affect the expression of a gene that encodes a JNKKK gene product, comprising: (a) applying a test compound to a test sample; (b) determining the expression level of at least one gene in cells of the test sample, wherein the gene comprises a nucleotide sequence selected from the group consisting of SEQ ID NOS: 1, 3, 5, 7, 9, 11 and 12; and (c) comparing the expression level of the gene in the test sample with that in a reference sample; wherein a specific change in the expression of the gene in the test sample as compared to the reference sample indicates that the test compound affects the expression of the gene. In a preferred embodiment, the method further comprises the step of applying a stress event to the test sample and determining the effect of the test compound on the gene expression response of the test sample to the stress event.

Still another aspect of the invention provides a method of screening for compounds that affect the activity of a JNKKK gene product, the method comprising: (a) applying a test compound to a test sample; and (b) determining the activity of a JNKKK gene product in the test sample versus a reference sample, wherein the JNKKK gene product comprises an amino acid sequence selected from the group consisting of: SEQ ID NOS: 2, 4, 6, 8,10 and 13; wherein a test compound that alters the JNKKK gene product activity in the test sample as compared to the reference sample is identified as a compound that affects the activity of the JNKKK gene product. In a preferred embodiment, the method further comprises the step of applying a stress event to the test sample and determining the effect of the test compound on the response of the test sample to the stress event.

4. BRIEF DESCRIPTION OF THE FIGURES

FIG. 1 is a schematic diagram illustrating the structure of the PAK5 gene.

Figure 2:
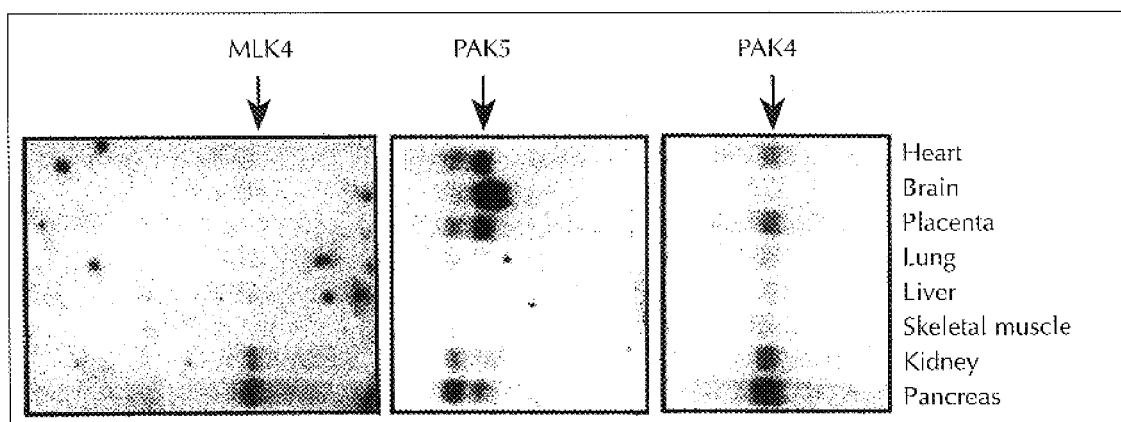

FIG. 2 is a Northern Blot illustrating the tissue-specific expression of MLK4, PAK4 and PAK5 genes. Messenger RNA was isolated from heart, brain, placenta, lung, liver, skeletal muscle, kidney and pancreas, run on a denaturing gel in the indicated lanes, and blotted to a membrane. The same blot was sequentially hybridized (after stripping between hybridizations) to labeled 150 base pair probes specific for MLK4, PAK4 and PAK5.

Figure 3A:
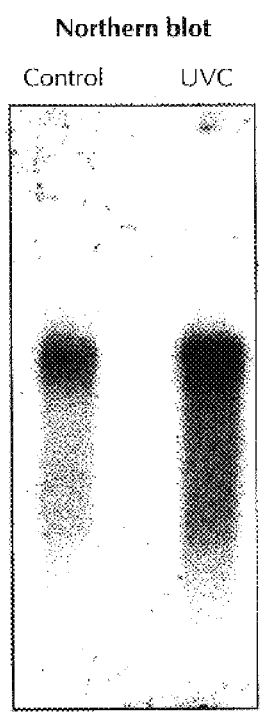

FIG. 3 shows the induction of YSK2 and PAK5 genes in response to ultraviolet radiation. FIG. 3A is a Northern blot of mRNA from keratinocytes untreated (control) or treated (control) with UV-C radiation for 5 days. The blot was hybridized to a 150 base pair probe specific for the. YSK2 gene.

Figure 3B:
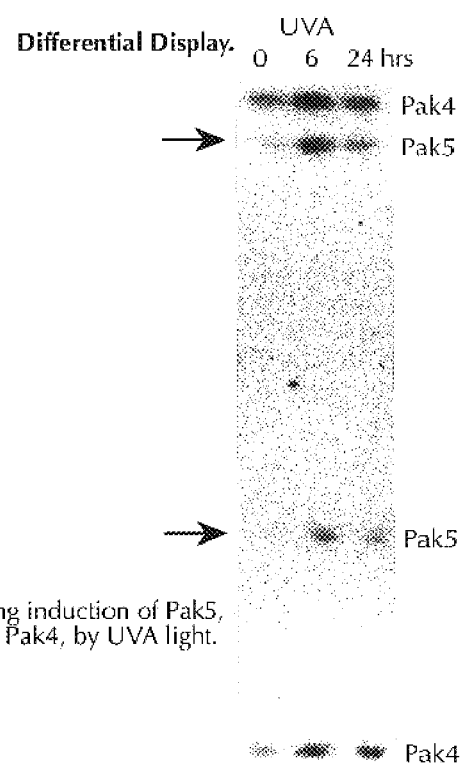

FIG. 3B shows a differential display experiment designed to examine any change in expression levels of the PAK4 and PAK5 genes in response to UV-A light. Keratinocytes were exposed to UV-A light for 0, 6 or 24 hours, harvested and mRNA analyzed. Bands corresponding the PAK4 and PAK5 message are indicated.

5. DETAILED DESCRIPTION OF THE INVENTION

The present invention relates to identification and characterization of polynucleotide molecules expressed in skin keratinocytes, which polynucleotide molecules encode JNKKK polypeptides. Because the kinase domains of JNKKKs are conserved in sequence, primers can be designed for reverse transcription-polymerase chain reaction (RT-PCR) detection of virtually all the JNKKKs expressed by a cell or cell type. In one embodiment, the primer pair 5'-ATGCA(CA)CANGA(CT)AT(ACT)AA(AG)-3' (SEQ ID NO:14) (forward) and 5'-GCNAC(CT) TCNGGNGCCATCCA-3' (SEQ ID NO:15) (reverse) can be used to detect novel JNKKKs. The product of using the primer pair is a common 150 bp segment. As discussed below in the Example sections, a primer pair was used to screen human epidermal keratinocyte mRNA, and polynucleotides encoding several novel JNKKKs were discovered. In addition, the present invention relates to the discovery that the JNKKKs encoded by these polynucleotides are involved in the cellular response to stress such as ultraviolet (UV) light. By way of example, the invention is described in the sections below for an isolated polynucleotide molecule comprising the nucleotide sequence of a portion of the MLK4 open reading frame (ORF) (SEQ ID NO:1); for an isolated polynucleotide molecule comprising the nucleotide sequence of a portion of the PAK4 ORF (SEQ ID NO:3); for an isolated polynucleotide molecule comprising the nucleotide sequence of a portion of the PAK5 ORF (SEQ ID NO:5); for another isolated polynucleotide molecule comprising the nucleotide sequence of a portion of the PAK5 gene (SEQ ID NO:7); for an isolated polynucleotide molecule comprising the nucleotide sequence of the cDNA encoding the PAK5 gene product (SEQ ID NO:9, ORF from nt 199–2244); for an isolated polynucleotide molecule comprising the nucleotide sequence of the PAK5 gene (SEQ ID NO:11, ORF from nt 6125–17433); and for an isolated polynucleotide molecule comprising the nucleotide sequence of a portion of the YSK2 ORF (SEQ ID NO:12).

5.1. Polynucleotide Molecules

As used herein, the terms "polynucleotide molecule," "polynucleotide sequence," "coding sequence" "open-reading frame (ORF)", and the like, are intended to refer to both DNA and RNA molecules, which can either be single-stranded or double-stranded. A coding sequence or ORF can include but is not limited to prokaryotic sequences, cDNA sequences, genomic DNA sequences, and chemically synthesized DNA and RNA sequences. A "gene product" is intended to refer to a product encoded by a gene, including the transcribed RNA message (including exons and introns), the spliced messenger RNA (mRNA), and the translated protein product encoded by the respective mRNA.

Production and manipulation of the polynucleotide molecules and oligonucleotide molecules disclosed herein are within the skill in the art and can be carried out according to recombinant techniques described, among other places, in Maniatis et al. 1989, Molecular Cloning, A Laboratory Manual, Cold Spring Harbor Laboratory Press, Cold Spring Harbor, N.Y.; Ausubel et al., 1989, Greene Publishing Associates & Wiley Interscience, NY; Sambrook et al., 1989, Molecular Cloning: A Laboratory Manual, 2d ed., Cold Spring Harbor Laboratory Press, Cold Spring Harbor, N.Y.; Innis et al. (eds), 1995, PCR Strategies, Academic Press, Inc., San Diego; and Erlich (ed), 1992, PCR Technology, Oxford University Press, New York, all of which are incorporated herein by reference.

5.1.1. MLK4-related Polynucleotide Molecules

The present invention provides an isolated polynucleotide molecule comprising a nucleotide sequence encoding a portion of a human MLK4-related gene product. In a preferred embodiment, the portion of the MLK4 gene product comprises the amino acid sequence of SEQ ID NO:2. In a non-limiting embodiment, the isolated polynucleotide molecule of the present invention comprises the nucleotide sequence of SEQ ID NO:1.

The present invention further provides an isolated polynucleotide molecule that is homologous to a polynucleotide molecule comprising the nucleotide sequence of SEQ ID NO:1. The term "homologous" when used in this respect means a polynucleotide molecule comprising a nucleotide sequence: (a) that encodes the same polypeptide as encoded by SEQ ID NO:1, but that includes one or more silent changes to the nucleotide sequence according to the degeneracy of the genetic code (i.e., a degenerate variant); or (b) that has at least about 70%, more preferably at least about 80%, and most preferably at least about 90% nucleotide sequence identity to the nucleotide sequence of SEQ ID NO:1, as determined by any standard nucleotide sequence identity algorithm such as BLASTN (GENBANK), and which hybridizes to the complement of a polynucleotide molecule comprising a nucleotide sequence that encodes a polypeptide comprising the amino acid sequence of SEQ ID NO:2 under moderately stringent conditions, i.e., hybridization to filter-bound DNA in 0.5 M NaHPO4, 7% sodium dodecyl sulfate (SDS), 1 mM EDTA at 65C, and washing in 0.2×SSC/0.1% SDS at 42° C. (see Ausubel et al. (eds.), 1989, Current Protocols in Molecular Biology, Vol. I, Green Publishing Associates, Inc., and John Wiley & Sons, Inc., New York, at p. 2.10.3), and is useful in practicing the invention. In a preferred embodiment, the homologous polynucleotide molecule hybridizes to the complement of a polynucleotide molecule comprising a nucleotide sequence that encodes a polypeptide comprising the amino acid sequence of SEQ ID NO:2 under highly stringent conditions, i.e., hybridization to filter-bound DNA in 0.5 M NaHPO4, 7% SDS, 1 mM EDTA at 65° C., and washing in 0.1×SSC/0.1% SDS at 68° C. (Ausubel et al., 1989, above), and is useful in practicing the invention. In a more preferred embodiment, the homologous polynucleotide molecule hybridizes under highly stringent conditions to the complement of a polynucleotide molecule consisting of the nucleotide sequence of SEQ ID NO:1, and is useful in practicing the invention.

As used herein, an MLK4-related polynucleotide molecule is "useful in practicing the invention" where the polynucleotide molecule: (i) encodes a peptide that can be used to generate antibodies that immunospecifically recognize the MLK4 gene product from a eukaryotic cell; or (ii) can detect the presence of the MLK4 transcript in a test sample; or (iii) can enable a method for altering the regulation or expression of the endogenous MLK4 gene (such as by gene activation or inactivation techniques, e.g., insertion of a transcriptional activator sequence into an intron, or deletion of one or more exons); or (iv) can be used to amplify a polynucleotide molecule comprising the nucleotide sequence of the MLK4 ORF in a eukaryotic cell using standard amplification techniques such as PCR. Such homologous polynucleotide molecules can include naturally occurring MLK4 genes present in eukaryotic species other than humans (and particularly in mammalian species, such as, for example, mouse, cow, sheep, guinea pig and rat), or in other human isolates, as well as mutated MLK4 alleles, whether naturally occurring, chemically synthesized, or genetically engineered.

The present invention further provides an isolated polynucleotide molecule comprising a nucleotide sequence that encodes a polypeptide having an amino acid sequence that is homologous to the amino acid sequence of SEQ ID NO:2. As used herein to refer to polypeptides having amino acid sequences that are homologous to the amino acid sequence of a portion of an MLK4 gene product from a human, the term "homologous" means a polypeptide comprising the amino acid sequence of SEQ ID NO:2, but in which one or more amino acid residues thereof has been conservatively substituted with a different amino acid residue, wherein the resulting amino acid sequence has at least about 70%, more preferably at least about 80%, and most preferably at least about 90% sequence identity to SEQ ID NO:2 wherein amino acid sequence identity is determined by any standard amino acid sequence identity algorithm, such as, e.g., BLASTP (GENBANK), where the resulting polypeptide is useful in practicing the invention. Conservative amino acid substitutions are well known in the art. Rules for making such substitutions include those described by Dayhof, M. D., 1978, Nat. Biomed. Res. Found., Washington, D.C., Vol. 5, Sup. 3, among others. More specifically, conservative amino acid substitutions are those that generally take place within a family of amino acids that are related in the acidity, or polarity of their side chains. Genetically encoded amino acids are generally divided into four groups: (1) acidic= aspartate, glutamate; (2) basic=lysine, arginine, histidine; (3) non-polar =alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan and tyrosine are also jointly dassified as aromatic amino acids. One or more replacements within any particular group, e.g., of a leucine with an isoleucine or valine, or of an aspartate with a glutamate, or of a threonine with a serine, or of any other amino acid residue with a structurally related amino acid residue, e.g., an amino acid residue with similar acidity, or polarity or with similarity in a combination thereof, will generally have an insignificant effect on the function of the polypeptide.

As used herein, an MLK4-related polypeptide is "useful in practicing the invention" where the polypeptide can be used to raise antibodies against an MLK4 gene product from a eukaryotic, preferably mammalian, and most preferably human cell or tissue, or to screen for compounds that modulate MLK4 activity or production in such a cell or tissue.

The present invention further provides an isolated polynucleotide molecule consisting of a nucleotide sequence that is a substantial portion of any of the aforementioned MLK4-related polynucleotide molecules of the present invention. As used herein, a "substantial portion" of an MLK4-related polynucleotide molecule means a polynucleotide molecule consisting of less than the full length of the nucleotide sequence of SEQ ID NO:1 or homologous polynucleotide molecule thereof, but comprising at least about 20%, and more preferably at least about 30%, of the length of said nucleotide sequence, and that is useful in practicing the invention, as usefulness is defined above for MLK4-related polynucleotide molecules. In a non-limiting embodiment, the substantial portion of the MLK4-related polynucleotide molecule consists of a nucleotide sequence that encodes a peptide fragment of a human MLK4 gene product of the present invention. A "peptide fragment" of an MLK4-related polypeptide refers to a polypeptide consisting of a sub-sequence of SEQ ID NO:2, which sub-sequence is useful in practicing the invention, as usefulness is defined above for MLK4-related polypeptides. As used herein, a "peptide fragment" is preferably at least about 15 amino acid residues, and more preferably at least about 30 amino acid residues in length.

The MLK4-related polynucleotide molecules disclosed herein can be used to express a portion of the human MLK4 gene product, to detect expression of an MLK4 gene product in a cell type or tissue, to prepare novel cell lines in which the MLK4 gene has been mutated (for example, altered or removed by homologous recombination), to create and express a dominant-negative MLK4, e.g., by mutating the ATP binding site, using well known techniques (see, e.g., Abo et al., below), and to identify MLK4 homolog genes in eukaryotic species other than humans, and particularly in other mammalian species, using known techniques. Thus, the present invention further provides an isolated polynucleotide molecule comprising a nucleotide sequence encoding an MLK4 homolog gene product. As used herein, an "MLK4 homolog gene product" is defined as a gene product encoded by an MLK4 homolog gene which, in turn, is defined as a gene from a different eukaryotic species other than human and which is recognized by those of skill in the art as a homolog of the human MLK4 gene based on a degree of sequence identity at the amino acid level of greater than about 70%.

Methods for identifying polynucleotide clones containing MLK4 homolog genes are known in the art. For example, a polynucleotide molecule comprising a portion of the human MLK4 ORF can be detectably labeled and used to screen a genomic library constructed from DNA derived from the organism of interest. The stringency of the hybridization conditions can be selected based on the relationship of the reference organism to the organism of interest. Requirements for different stringency conditions are well known to those of skill in the art, and such conditions will vary predictably depending on the specific organisms from which the library and the labeled sequences are derived. Genomic DNA libraries can be screened for MLK4 homolog gene coding sequences using the techniques set forth, among other places, in Benton and Davis, 1977, Science 196:180, for bacteriophage libraries, and in Grunstein and Hogness, 1975, Proc. Natl. Acad. Sci. USA, 72:3961–3965, for plasmid libraries, which publications are incorporated herein by reference. Polynucleotide molecules having nucleotide sequences known to include a portion of the MLK4 ORF, as shown in SEQ ID NO:1, or oligonucleotide molecules representing portions thereof, can be used as probes in these screening experiments. Alternatively, oligonucleotide probes can be synthesized that correspond to nucleotide sequences deduced from the amino acid sequence of the purified MLK4 gene product.

Clones identified as containing MLK4 homolog gene coding sequences can be tested for appropriate biological function. For example, the clones can be subjected to sequence analysis in order to identify a suitable reading frame, as well as initiation and termination signals. The cloned DNA sequence can then be inserted into an appropriate expression vector which is then transformed into cells (such as human cells) that have been rendered MLK4 null to test for complementation. Transformed host cells can then be analyzed for MLK4 signal transduction.

5.1.2. PAK4-related Polynucl Otide Molecules

The present invention further provides an isolated polynucleotide molecule comprising a nucleotide sequence encoding a portion of a human PAK4 gene product. In a preferred embodiment, the portion of the PAK4 gene product comprises the amino acid sequence of SEQ ID NO:4. In a non-limiting embodiment, the isolated polynucleotide molecule of the present invention comprises the nucleotide sequence of SEQ ID NO:3.

The present invention further provides an isolated polynucleotide molecule that is homologous to a polynucleotide molecule comprising the nucleotide sequence of SEQ ID NO:3. The term "homologous" when used in this respect means a polynucleotide molecule comprising a nucleotide sequence: (a) that encodes the same polypeptide as encoded by SEQ ID NO:3, but that includes one or more silent changes to the nucleotide sequence according to the degeneracy of the genetic code; or (b) that has at least about 70%, more preferably at least about 80%, and most preferably at least about 90% nucleotide sequence identity to the nucleotide sequence of SEQ ID NO:3, as determined by any standard nucleotide sequence identity algorithm such as BLASTN (GENBANK) and hybridizes to the complement of a polynucleotide molecule comprising a nucleotide sequence that encodes a polypeptide comprising the amino acid sequence of SEQ ID NO:4 under moderately stringent conditions, i.e., hybridization to filter-bound DNA in 0.5 M NaHPO4, 7% SDS, 1 mM EDTA at 65° C., and washing in 0.2×SSC/0.1% SDS at 42° C. (Ausubel et al., 1989, above), and is useful in practicing the invention. In a preferred embodiment, the homologous polynucleotide molecule hybridizes to the complement of a polynucleotide molecule comprising a nucleotide sequence that encodes a polypeptide comprising the amino acid sequence of SEQ ID NO:4 under highly stringent conditions, i.e., hybridization to filter-bound DNA in 0.5 M NaHPO4, 7% SDS, 1 mM EDTA at 65° C., and washing in 0.1×SSC/0.1% SDS at 68° C. (Ausubel et al., 1989, above), and is useful in practicing the invention. In a more preferred embodiment, the homologous polynucleotide molecule hybridizes under highly stringent conditions to the complement of a polynucleotide molecule comprising the nucleotide sequence of SEQ ID NO:3, and is useful in practicing the invention.

As used herein, a PAK4-related polynucleotide molecule is "useful in practicing the invention" where the polynucleotide molecule: (i) encodes a peptide that can be used to generate antibodies that immunospecifically recognize the PAK4 gene product from a eukaryotic cell; or (ii) can detect the presence of the PAK4 transcript in a test sample; or (iii) can enable a method for altering the regulation or expression of the endogenous PAK4 gene (such as by gene activation or inactivation techniques, e.g., insertion of a transcriptional activator sequence into an intron, or deletion of one or more exons); or (iv) can be used to amplify a polynucleotide molecule comprising the nucleotide sequence of the PAK4 ORF in a eukaryotic cell using standard amplification techniques such as PCR. Such homologous polynucleotide molecules can include naturally occurring PAK4 genes present in eukaryotic species other than humans (and particularly in mammalian species, such as, for example, mouse, cow, sheep, guinea pig and rat), or in other human isolates, as well as mutated PAK4 alleles, whether naturally occurring, chemically synthesized, or genetically engineered.

The present invention further provides an isolated polynucleotide molecule comprising a nucleotide sequence that encodes a polypeptide having an amino acid sequence that is homologous to the amino acid sequence of SEQ ID NO:4. As used herein to refer to polypeptides having amino acid sequences that are homologous to the amino acid sequence of a PAK4 gene product from a human cell, the term "homologous" means a polypeptide comprising the amino acid sequence of SEQ ID NO:4, but in which one or more amino acid residues thereof has been conservatively substituted with a different amino acid residue, as conservative amino acid substitutions are defined above, wherein the resulting amino acid sequence has at least about 70%, more preferably at least about 80%, and most preferably at least about 90% sequence identity to SEQ ID NO:4, as determined, e.g., using the BLASTP algorithm (GENBANK), where the resulting polypeptide is useful in practicing the invention.

As used herein, a PAK4-related polypeptide is "useful in practicing the invention" where the polypeptide can be used to raise antibodies against a PAK4 gene product from a eukaryotic, preferably mammalian, and most preferably human, cell or tissue, or to screen for compounds that modulate PAK4 activity or production in such a cell or tissue.

The present invention further provides an isolated polynucleotide molecule consisting of a nucleotide sequence that is a substantial portion of any of the aforementioned PAK4-related polynucleotide molecules of the present invention. As used herein, a "substantial portion" of a PAK4-related polynucleotide molecule means a polynucleotide molecule consisting of less than the full length of SEQ ID NO:3 or homologous polynucleotide molecule thereof, but comprising at least about 20%, and more preferably at least about 30%, of the length of said nucleotide sequence, and that is useful in practicing the invention, as usefulness is defined above for PAK4-related polynucleotide molecules. In a non-limiting embodiment, the substantial portion of the PAK4-related polynucleotide molecule consists of a nucleotide sequence that encodes a peptide fragment of a human PAK4 gene product of the present invention. A "peptide fragment" of a PAK4-related polypeptide refers to a polypeptide consisting of a sub-sequence of SEQ ID NO:4, which sub-sequence is useful in practicing the invention, as usefulness is defined above for PAK4-related polypeptides. Peptide fragments of the invention are preferably at least about 15 amino acid residues, and more preferably at least about 30 amino acid residues in length.

The PAK4-related polynucleotide molecules disclosed herein can be used to express a portion of the human PAK4 gene product, to detect expression of a PAK4 gene product in a cell type or tissue, to prepare novel cell lines in which the PAK4 gene has been mutated (for example, altered or removed by homologous recombination), to create and express a dominant-negative PAK4, e.g., by mutating the ATP binding site, using well known techniques (see, e.g., Abo et al., below), and to identify PAK4 homolog genes in eukaryotic species other than humans, and particularly in other mammalian species, using known techniques. Thus, the present invention further provides an isolated polynucleotide molecule comprising a nucleotide sequence encoding a PAK4 homolog gene product. As used herein, a "PAK4 homolog gene product" is defined as a gene product encoded by a PAK4 homolog gene which, in turn, is defined as a gene from a different eukaryotic species other than human and which is recognized by those of skill in the art as a homolog of the human PAK4 gene based on a degree of sequence identity at the amino acid level of greater than about 70%. Methods for identifying polynucleotide clones containing PAK4 homolog genes are known in the art as described above.

5.1.3. PAK5-related Polynucleotide Molecules

The present invention further provides an isolated polynucleotide molecule comprising a nucleotide sequence encoding a portion of a human PAK5 gene product. In a preferred embodiment, the portion of the PAK5 gene product comprises the amino acid sequence of SEQ ID NO:6. In a non-limiting embodiment, the isolated polynucleotide molecule encoding the amino acid sequence of SEQ ID NO:6 comprises the nucleotide sequence of SEQ ID NO:5. In another preferred embodiment, the portion of the PAK5 gene product comprises the amino acid sequence of SEQ ID NO:8. In a non-limiting embodiment, the isolated polynucleotide molecule encoding the amino acid sequence of SEQ ID NO:8 comprises the nucleotide sequence of SEQ ID NO:7. Still another non-limiting embodiment of the invention is the sequence of any one of the exons of the PAK5 genomic DNA (see SEQ ID NO:7). A further non-limiting embodiment of the invention is the sequence of any one of the introns of the PAK5 genomic DNA.

The present invention further provides an isolated polynucleotide molecule comprising the cDNA nucleotide sequence of SEQ ID NO:9 (ORF from nt 199–2244) encoding a complete human PAK5 gene product. The present invention further provides an isolated polynucleotide molecule comprising the nucleotide sequence of SEQ ID NO:11 (ORF from nt 6125–17433), which represents the human PAK5 gene.

The present invention further provides an isolated polynucleotide molecule that is homologous to a polynucleotide molecule comprising a nucleotide sequence encoding a portion of a PAK5 gene product of the present invention. The term "homologous" when used in this respect means a polynucleotide molecule comprising a nucleotide sequence: (a) that encodes the same polypeptide as encoded by SEQ ID NO:5, SEQ ID NO:7, SEQ ID NO:9 or SEQ ID NO:11, but that includes one or more silent changes to the nucleotide sequence according to the degeneracy of the genetic code; or (b) that has at least about 70%, more preferably at least about 80%, and most preferably at least about 90% nucleotide sequence identity to the nucleotide sequence of SEQ ID NO:5 or SEQ ID NO:7, or to the ORF of SEQ ID NO:9 or SEQ ID NO:11, as determined by any standard nucleotide sequence identity algorithm such as BLASTN (GENBANK), and hybridizes to the complement of a polynucleotide molecule comprising a nucleotide sequence that encodes a polypeptide comprising the amino acid sequence of SEQ ID NO:6, SEQ ID NO:8, or SEQ ID NO:10 under moderately stringent conditions, i.e., hybridization to filter-bound DNA in 0.5 M NaHPO4, 7% SDS, 1 mM EDTA at 65° C., and washing in 0.2×SSC/0.1% SDS at 42° C. (Ausubel et al., 1989, above), and is useful in practicing the invention. In a preferred embodiment, the homologous polynucleotide molecule hybridizes to the complement of a polynucleotide molecule comprising a nucleotide sequence that encodes a polypeptide comprising the amino acid sequence of SEQ ID NO:6, SEQ ID NO:8, or SEQ ID NO:10 under highly stringent conditions, i.e., hybridization to filter-bound DNA in 0.5 M NaHPO4, 7% SDS, 1 mM EDTA at 65° C., and washing in 0.1×SSC/0.1% SDS at 68° C. (Ausubel et al., 1989, above), and is useful in practicing the invention. In a more preferred embodiment, the homologous polynucleotide molecule hybridizes under highly stringent conditions to the complement of a polynucleotide molecule consisting of the nucleotide sequence of SEQ ID NO:5 or SEQ ID NO:7, or the ORF of SEQ ID NO:9 or SEQ ID NO:11, and Is useful in practicing the invention.

As used herein, a PAK5-related polynucleotide molecule is "useful in practicing the invention" where the polynucleotide molecule: (i) encodes a peptide that can be used to generate antibodies that immunospecifically recognize the PAK5 gene product from a eukaryotic cell; or (ii) can detect the presence of the PAK5 transcript in a test sample; or (iii) can enable a method for altering the regulation or expression of the endogenous PAK5 gene (such as by gene activation or inactivation techniques, e.g., insertion of a transcriptional activator sequence into an intron, or deletion of one or more exons); or (iv) can be used to amplify a polynucleotide molecule comprising the nucleotide sequence of the PAK5 ORF in a eukaryotic cell using standard amplification techniques such as PCR. Such homologous polynucleotide molecules can include naturally occurring PAK5 genes present in eukaryotic species other than humans (and particularly in mammalian species, such as, for example, mouse, cow, sheep, guinea pig and rat), or in other human isolates, as well as mutated PAK5 alleles, whether naturally occurring, chemically synthesized, or genetically engineered.

The present invention further provides an isolated polynucleotide molecule comprising a nucleotide sequence that encodes a polypeptide having an amino acid sequence that is homologous to the amino acid sequence of SEQ ID NO:6, SEQ ID NO:8 or SEQ ID NO:10. As used herein to refer to polypeptides having amino acid sequences that are homologous to the amino acid sequence of a PAK5 gene product from a human cell, the term "homologous" means a polypeptide comprising the amino acid sequence of SEQ ID NO:6, SEQ ID NO:8 or SEQ ID NO:10, but in which one or more amino acid residues thereof has been conservatively substituted with a different amino acid residue, as conservative amino acid substitutions are defined above, wherein the resulting amino acid sequence has at least about 70%, more preferably at least about 80%, and most preferably at least about 90% sequence identity to SEQ ID NO:6, SEQ ID NO:8 or SEQ ID NO:10, as determined, e.g., using the BLASTP algorithm (GENBANK), and where the resulting polypeptide is useful in practicing the invention.

As used herein, a PAK5-related polypeptide is "useful in practicing the invention" where the polypeptide can be used to raise antibodies against a PAK5 gene product from a eukaryotic, preferably mammalian, and most preferably human, cell or tissue, or to screen for compounds that modulate PAK5 activity or production in such a cell.

The present invention further provides an isolated polynucleotide molecule consisting of a nucleotide sequence that is a substantial portion of any of the aforementioned PAK5-related polynucleotide molecules of the present invention. As used herein, a "substantial portion" of a PAK5-related polynucleotide molecule means a polynucleotide molecule consisting of less than the full length of SEQ ID NO:5, SEQ ID NO:7, SEQ ID NO:9 (from nt 199–2244) or SEQ ID NO:11 (from nt 6125–17433) or homologous polynucleotide molecule thereof, but comprising at least about 20%, and more preferably at least about 30%, the length of said nucleotide sequence, and that is useful in practicing the invention, as usefulness is defined above for PAK5-related polynucleotide molecules. In a non-limiting embodiment, the substantial portion of the PAK5-related polynucleotide molecule consists of a nucleotide sequence that encodes a peptide fragment of a human PAK5 gene product of the present invention. A "peptide fragment" of a PAK5-related polypeptide refers to a polypeptide consisting of a sub-sequence of SEQ ID NO:6, SEQ ID NO:8 or SEQ ID NO:10, which sub-sequence is useful in practicing the invention, as usefulness is defined above for PAK5-related polypeptides. Peptide fragments of the invention are preferably at least about 15 amino acid residues, and more preferably at least about 30 amino acid residues in length.

The PAK5-related polynucleotide molecules disclosed herein can be used to express a portion of the PAK5 gene product, to detect expression of a PAK5 gene in a cell or tissue, to prepare novel cell lines in which the PAK5 gene has been mutated (for example, altered or removed by homologous recombination), to create and express a dominant-negative PAK5 by mutating the ATP binding site using well known techniques (see, e.g., Abo et al., below), and to identify PAK5 homolog genes in other eukaryotic species or cell types using standard techniques. Thus, the present invention further provides an isolated polynucleotide molecule comprising a nucleotide sequence encoding a PAK5 homolog gene product. As used herein, a "PAK5 homolog gene product" is defined as a gene product encoded by a PAK5 homolog gene which, in turn, is defined as a gene from a eukaryotic species other than human, and which is recognized by those of skill in the art as a homolog of the human PAK5 gene based on a degree of sequence identity at the amino acid level of greater than about 80%. Methods for identifying polynucleotide clones containing PAK5 homolog genes are known in the art, as described above.

5.1.4. YSK2-related Polynucleotide Molecules

The present invention further provides an isolated polynucleotide molecule comprising a nucleotide sequence encoding a portion of a YSK2 gene product from a human cell. In a preferred embodiment, the YSK2 gene product comprises the amino acid sequence of SEQ ID NO:13. In a non-limiting embodiment, the isolated polynucleotide molecule of the present invention comprises the nucleotide sequence of SEQ ID NO:12.

The present invention further provides an isolated polynucleotide molecule that is homologous to a polynucleotide molecule comprising a nucleotide sequence encoding a portion of the YSK2 gene product of the present invention. The term "homologous" when used in this respect means a polynucleotide molecule comprising a nucleotide sequence: (a) that encodes the same polypeptide as encoded by SEQ ID NO:12, but that includes one or more silent changes to the nucleotide sequence according to the degeneracy of the genetic code; or (b) that has at least about 70%, more preferably at least about 80%, and most preferably at least about 90% nucleotide sequence identity to the nucleotide sequence of SEQ ID NO:12, as determined by any standard nucleotide sequence identity algorithm such as BLASTN (GENBANK), and hybridizes to the complement of a polynucleotide molecule comprising a nucleotide sequence that encodes a polypeptide comprising the amino acid sequence of SEQ ID NO:13 under moderately stringent conditions, i.e., hybridization to filter-bound DNA in 0.5 M NaHPO4, 7% SDS, 1 mM EDTA at 65° C., and washing in 0.2×SSC/ 0.1% SDS at 42° C. (Ausubel et al., 1989, above), and encodes at least the first 6 amino acid residues of SEQ ID NO:13 and is useful in practicing the invention. In a preferred embodiment, the homologous polynucleotide molecule hybridizes to the complement of a polynucleotide molecule comprising a nucleotide sequence that encodes a polypeptide comprising the amino acid sequence of SEQ ID NO:13 under highly stringent conditions, i.e., hybridization to filter-bound DNA in 0.5 M NaHPO4, 7% SDS, 1 mM EDTA at 65° C., and washing in 0.133 SSC/0.1% SDS at 68° C. (Ausubel et al., 1989, above), and encodes at least the first 6 amino acid residues of SEQ ID NO:13, and is useful in practicing the invention. In a more preferred embodiment, the homologous polynucleotide molecule hybridizes under highly stringent conditions to the complement of a polynucleotide molecule comprising the nucleotide sequence of SEQ ID NO:12, and encodes at least the first 6 amino acid residues of SEQ ID NO:13, and is useful in practicing the invention.

As used herein, a YSK2-related polynucleotide molecule is "useful in practicing the invention" where the polynucleotide molecule: (i) encodes a peptide that can be used to generate antibodies that immunospecifically recognize the YSK2 gene product from a eukaryotic cell; or (ii) can detect the presence of the YSK2 transcript in a test sample; or (iii) can enable a method for altering the regulation or expression of the endogenous YSK2 gene (such as by gene activation or inactivation techniques, e.g., insertion of a transcriptional activator sequence into an intron, or deletion of one or more exons); or (iv) can be used to amplify a polynucleotide molecule comprising the nucleotide sequence of the YSK2 ORF in a eukaryotic cell using standard amplification techniques such as PCR. Such homologous polynucleotide molecules can include naturally occurring YSK2 genes present in eukaryotic species other than humans (and particularly in mammalian species, such as, for example, mouse, cow, sheep, guinea pig and rat), or in other human isolates, as well as mutated YSK2 alleles, whether naturally occurring, chemically synthesized, or genetically engineered.

The present invention further provides an isolated polynucleotide molecule comprising a nucleotide sequence that encodes a polypeptide having an amino acid sequence that is homologous to the amino acid sequence of SEQ ID NO:13. As used herein to refer to polypeptides having amino acid sequences that are homologous to the amino acid sequence of a YSK2 gene product from a human cell, the term "homologous" means a polypeptide comprising the amino acid sequence of SEQ ID NO:13, but in which one or more amino acid residues thereof has been conservatively substituted with a different amino acid residue, as conservative amino acid substitutions are defined above, wherein the resulting amino acid sequence has at least about 70%, more preferably at least about 80%, and most preferably at least about 90% sequence identity to SEQ ID NO:13, as determined, e.g., using the BLASTP algorithm (GENBANK), and which encodes at least the first 6 amino acid residues of SEQ ID NO:13 and where the resulting polypeptide is useful in practicing the invention.

As used herein, a YSK2-related polypeptide is "useful in practicing the invention" where the polypeptide can be used to raise antibodies against a YSK2 gene product from a eukaryotic, preferably mammalian, and most preferably human, cell or tissue, or to screen for compounds that modulate YSK2 activity or production in such a cell or tissue.

The present invention further provides an isolated polynucleotide molecule consisting of a nucleotide sequence that is a substantial portion of any of the aforementioned YSK2-related polynucleotide molecules of the present invention. As used herein, a "substantial portion" of a YSK2-related polynucleotide molecule means a polynucleotide molecule consisting of less than the full length of SEQ ID NO:12 or homologous polynucleotide molecule thereof, but comprising at least about 20%, and more preferably at least about 30%, the length of said nucleotide sequence, and encoding at least the first 6 amino acid residues of SEQ ID NO:13 and that is useful in practicing the invention, as usefulness is defined above for YSK2-related polynucleotide molecules. In a non-limiting embodiment, the substantial portion of the YSK2-related polynucleotide molecule consists of a nucleotide sequence that encodes a peptide fragment of a YSK2 gene product of the present invention. A "peptide fragment" of a YSK2-related polypeptide refers to a polypeptide consisting of a sub-sequence of the amino acid sequence of SEQ ID NO:13, yet contains the sequence of residues 1 to 6 of SEQ ID NO: 13, and which sub-sequence is useful in practicing the invention, as usefulness is defined above for YSK2-related polypeptides. Peptide fragments of the invention are preferably at least about 15 amino acid residues, and more preferably at least about 30 amino acid residues in length.

The YSK2-related polynucleotide molecules disclosed herein can be used to express a portion of the human YSK2 gene product, to detect expression of a YSK2 gene product in a cell type or tissue, to prepare novel cell lines in which the YSK2 gene has been mutated (for example, altered or removed by homologous recombination), to create and express a dominant-negative YSK2 by mutating the ATP binding site using well known techniques (see, e.g., Abo et al., below), and to identify YSK-2 homolog genes in other eukaryotic species or cell types, as described above. As used herein, a "YSK2 homolog gene product" is defined as a gene product encoded by a YSK2 homolog gene which, in turn, is defined as a gene from a eukaryotic species other than human, and which is recognized by those of skill in the art as a homolog of the human YSK2 gene based on a degree of sequence identity at the amino acid level of greater than about 80%. Methods for identifying polynucleotide clones containing YSK2 homolog genes are known in the art, as described above.

5.2. Oligonucleotide Molecules

The present invention further provides oligonucleotide molecules that hybridize to any of the aforementioned polynucleotide molecules of the present invention, or that hybridize to a polynucleotide molecule having a nucleotide sequence that is the complement of any of the aforementioned polynucleotide molecules of the present invention. Such oligonucleotide molecules are preferably at least about 10 nucleotides in length, and more preferably at least about 20 nucleotides in length, and can hybridize to one or more of the aforementioned polynucleotide molecules under moderately or highly stringent conditions. For shorter oligonucleotide molecules, an example of highly stringent conditions includes washing in 6×SSC/0.5% sodium pyrophosphate at about 37° C. for ~14-base oligos, at about 48° C. for ~17-base oligos, at about 55° C. for ~20-base oligos, and at about 60° C. for ~23-base oligos. For longer oligonucleotide molecules (i.e., greater than about 100 nts), examples of moderately and highly stringent conditions are described in Section 5.1.1 above for homologous polynucleotide molecules. Hybridization conditions can be appropriately adjusted as known in the art, depending upon the particular oligonucleotide molecules utilized.

In a preferred embodiment, an oligonucleotide molecule of the present invention hybridizes under highly stringent conditions to a polynucleotide molecule having a nucleotide sequence selected from the group consisting of SEQ ID NOs:1, 3, 5, 7, 9, 11 or 12, or to a polynucleotide molecule having a nucleotide sequence that is the complement of a nucleotide sequence selected from the group consisting of SEQ ID NOs:1, 3, 5, 7, 9, 11 or 12.

The oligonucleotide molecules of the present invention are useful for a variety of purposes, including as primers in amplifying a MLK4, PAK4, PAK5 or YSK2 gene product-encoding polynucleotide molecule, or as anti-sense molecules useful in regulating expression of JNKKK genes and gene products. Amplification can be carried out using suitably designed oligonucleotide molecules in conjunction with standard techniques, such as the polymerase chain reaction (PCR), although other amplification techniques known in the art, e.g., the ligase chain reaction, can also be used. For example, for PCR, a mixture comprising suitably designed primers, a template comprising the nucleotide sequence to be amplified, and appropriate PCR enzymes and buffers, is prepared and processed according to standard protocols to amplify a specific MLK4-, PAK4-, PAK5-, or YSK2-related polynucleotide sequence of the template.

5.3. Recombinant Expression Systems
5.3.1. Expression Vectors

The present invention further provides recombinant cloning vectors and recombinant expression vectors comprising a polynucleotide molecule of the present invention, which vectors are useful in cloning or expressing said polynucleotide molecules, including polynucleotide molecules comprising portions of the MLK4, PAK4, PAK5 or YSK2 ORFs, or the entire PAK5 ORF, of the present invention.

The following description is intended to apply to all of the aforementioned polynucleotide molecules and polypeptides of the present invention, including polynucleotide molecules comprising portions of the MLK4, PAK4, PAK5 or YSK2 ORFs, the entire PAK5 ORF, and their gene products, and all homologous polynucleotide molecules, homologous polypeptides, substantial portions of such polynucleotide molecules, and peptide fragments of such gene products and polypeptides, as defined above, unless otherwise indicated.

Recombinant vectors of the present invention, particularly expression vectors, are preferably constructed so that the coding sequence for the polynucleotide molecule of the present invention is in operative association with one or more regulatory elements necessary for transcription and translation of the coding sequence to produce a polypeptide. As used herein, the term "regulatory element" includes but is not limited to nucleotide sequences of inducible and noninducible promoters, enhancers, operators and other elements known in the art that serve to drive and/or regulate expression of polynucleotide coding sequences. Also, as used herein, the coding sequence is in "operative association" with one or more regulatory elements where the regulatory elements effectively regulate and allow for the transcription of the coding sequence or the translation of its mRNA, or both.

Typical plasmid vectors that can be engineered to contain a polynucleotide molecule of the present invention include pCR-Blunt, pCR2.1 (Invitrogen), and pGEM3Zf (Promega), among many others. Additionally, vectors particularly designed for expression in eukaryotic cells, such as mammalian cells, are commercially available from Invitrogen (San Diego, Calif.) and Promega.

The regulatory elements of these vectors can vary in their strength and specificities. Depending on the host/vector system utilized, any of a number of suitable transcription and translation elements can be used. Non-limiting examples of transcriptional regulatory regions or promoters for bacteria include the β-gal promoter, the T7 promoter, the TAC promoter, lambda left and right promoters, trp and lac promoters, and the trp-lac fusion promoters. Non-limiting examples of transcriptional regulatory regions or promoters for eukaryotic cells include viral regulatory regions such as, for example, the SV40 early promoter region, the herpes thymidine kinase promoter, the cytomegalovirus (CMV) promoter, and the mouse mammary tumor virus control region, tissue specific or inducible promoters from endogenous eukaryotic genes such as, for example, the albumin promoter, myosin light chain-2 promoter, the insulin promoter, the metallothionein promoter, and fungal promoters such as, for example, the gal 4 promoter, the alcohol dehydrogenase promoter, the phosphoglycerol kinase promoter, and the mating factor promoters, to name just a few.

Methods are well-known in the art for constructing recombinant vectors containing particular coding sequences in operative association with appropriate regulatory elements, and any of these can be used to practice the present invention. These methods include in vitro recombinant techniques, synthetic techniques, and in vivo genetic recombination. See, e.g., the techniques described in Maniatis et al., 1989, above: Ausubel et al., 1989, above; Sambrook et al., 1989, above; Innis et al., 1995, above; and Erlich, 1992, above.

Fusion protein expression vectors can be used to express an MLK4, PAK4, PAK5 or YSK2 gene product-fusion protein. The purified fusion protein can be used to raise antisera against the MLK4, PAK4, PAK5 or YSK2 gene product, to study the biochemical properties of the MLK4, PAK4, PAK5 or YSK2 gene product, to engineer the MLK4, PAK4, PAK5 or YSK2 fusion proteins with different biochemical activities, or to aid in the identification or purification of the expressed MLK4, PAK4, PAK5 or YSK2 gene product in recombinant expression systems. Possible fusion protein expression vectors include but are not limited to vectors incorporating sequences that encode β-galactosidase and trpE fusions, maltose binding protein fusions, glutathione-S-transferase fusions and polyhistidine fusions (carrier regions).

MLK4, PAK4, PAK5 or YSK2 fusion proteins can be engineered to comprise a region useful for purification. For example, MLK4-, PAK4-, PAK5- and YSK2-maltose-binding protein fusions can be purified using amylose resin; MLK4-, PAK4-, PAK5- and YSK2-glutathione-S-transferase fusion proteins can be purified using glutathione-agarose beads; and MLK4-, PAK4-, PAK5- and YSK2-polyhistidine fusions can be purified using divalent nickel resin. Alternatively, antibodies against a carrier protein or peptide can be used for affinity chromatography purification of the fusion protein. For example, a nucleotide sequence coding for the target epitope of a monoclonal antibody can be engineered into the expression vector in operative association with the regulatory elements and situated so that the expressed epitope is fused to the MLK4, PAK4, PAK5 or YSK2 polypeptide. For example, a nucleotide sequence coding for the FLAG™ epitope tag (International Biotechnologies Inc.), which is a hydrophilic marker peptide, can be inserted by standard techniques into the expression vector at a point corresponding to the amino or carboxyl terminus of the MLK4, PAK4, PAK5 or YSK2 polypeptide. The expressed MLK4, PAK4, PAK5 or YSK2 polypeptide-FLAG™ epitope fusion product can then be detected and affinity-purified using commercially available anti-FLAG™ antibodies.

The expression vector encoding the MLK4, PAK4, PAK5 or YSK2 fusion protein can also be engineered to contain sequences that encode specific protease cleavage sites so that the expressed MLK4, PAK4, PAK5 or YSK2 polypeptide can be released from the carrier region or fusion partner by treatment with a specific protease. For example, the fusion protein vector can include DNA sequences encoding thrombin or factor Xa cleavage sites, among others.

A signal sequence upstream from and in reading frame with the MLK4, PAK4, PAK5 or YSK2 ORF can be engineered into the expression vector by known methods to direct the trafficking and secretion of the expressed gene product. Non-limiting examples of signal sequences include those from α factor, immunoglobulins, outer membrane proteins, penicillinase, and T-cell receptors, among others.

To aid in the selection of host cells transformed or transfected with cloning or expression vectors of the present invention, the vector can be engineered to further comprise a coding sequence for a reporter gene product or other selectable marker. Such a coding sequence is preferably in operative association with regulatory element coding sequences, as described above. Reporter genes that can be useful in the invention are well known in the art and include those encoding green fluorescent protein, luciferase, xylE, and tyrosinase, among others. Nucleotide sequences encoding selectable markers are well known in the art, and include those that encode gene products conferring resistance to antibiotics or anti-metabolites, or that supply an auxotrophic requirement. Examples of such sequences include those that encode resistance to methotrexate, G418 or mycophenolic acid, among many others.

5.3.2. Host Cells

The present invention further provides transformed host cells comprising a polynucleotide molecule or recombinant vector of the invention, and novel strains or cell lines derived therefrom. Host cells useful in the practice of the invention are preferably human cells, although other eukaryotic cells or prokaryotic cells can also be used. Such other transformed host cells typically include but are not limited to microorganisms, such as bacteria transformed with recombinant bacteriophage DNA, plasmid DNA or cosmid DNA vectors, or yeast transformed with recombinant vectors, among others.

Appropriate host cells can be chosen that modify and process the gene product in the specific fashion desired. Different host cells have characteristic mechanisms for the translational and post-translational processing and modification (e.g., glycosylation, phosphorylation) of proteins. For example, expression in a bacterial system can be used to produce an unglycosylated protein product. Expression and secretion in yeast can produce a glycosylated protein product. Expression in mammalian cells can be used to ensure "native" processing of a protein product. Further, different vector/host expression systems can affect processing reactions to different degrees.

Preferred bacterial cells as host cells are strains of *E. coli*, e.g., for cloning or expression purposes. A strain of *E. coli* adapted to growth in culture and for cloning techniques can typically be used, such as, e.g., the DH5α strain, which is available either from the American Type Culture Collection (ATCC), Rockville, Md. USA (Accession No. 31343) or from commercial sources (Stratagene). Preferred eukaryotic host cells include human cells, and in particular keratinocytes, although other mammalian cells and yeast cells or insect cells can also be utilized effectively.

The recombinant expression vector of the invention is preferably transformed or transfected into one or more host cells of a substantially homogeneous culture of cells. The expression vector is generally introduced into host cells in accordance with known techniques, such as, e.g., by protoplast transformation, calcium phosphate precipitation, calcium chloride treatment, microinjection, electroporation, transfection by contact with a recombined virus, liposome-mediated transfection, DEAE-dextran transfection, transduction, conjugation, or microprojectile bombardment. Selection of transformants can be conducted by standard procedures, such as by selecting for cells expressing a selectable marker, e.g., antibiotic resistance, associated with the recombinant vector, as described above.

Once the expression vector is introduced into the host cell, the integration and maintenance of the MLK4-, PAK4-, PAK5- or YSK2-related coding sequence, either in the host cell chromosome or episomally, can be confirmed by standard techniques, e.g., by Southern hybridization analysis, restriction enzyme analysis, PCR analysis, including reverse transcriptase PCR (rt-PCR), or by immunological assay to detect the expected gene product. Host cells containing and/or expressing the recombinant MLK4-, PAK4-, PAK5- or YSK2-related coding sequence can be identified by any of at least four general approaches which are well-known in the art, including: (i) DNA-DNA, DNA-RNA, or RNA-antisense RNA hybridization; (ii) detecting the presence of "marker" gene functions; (iii) assessing the level of transcription as measured by the expression of MLK4-, PAK4-, PAK5- or YSK2-specific mRNA transcripts in the host cell; and (iv) detecting the presence of mature polypeptide product as measured, e.g., by immunoassay.

5.3.3. Expression and Characterization of JNKKK Polypeptides

Once the MLK4-, PAK4-, PAK5- or YSK2-related coding sequence has been stably introduced into an appropriate host cell, the transformed host cell is clonally propagated, and the resulting cells are grown under conditions conducive to the maximum production of the MLK4-, PAK4-, PAK5- or YSK2-related gene products. Such conditions typically include growing cells to high density. Where the expression vector comprises an inducible promoter, appropriate induction conditions such as, e.g., temperature shift, exhaustion of nutrients, addition of gratuitous inducers (e.g., analogs of carbohydrates, such as isopropyl-β-D-thiogalactopyranoside (IPTG)), accumulation of excess metabolic by-products, or the like, are employed as needed to induce expression.

Where the expressed MLK4-, PAK4-, PAKS- or YSK2-related gene product is retained inside the host cells, the cells are harvested and lysed, and the product is isolated and purified from the lysate under extraction conditions known in the art to minimize protein degradation such as, e.g., at 4° C., or in the presence of protease inhibitors, or both. Where the expressed MLK4-, PAK4-, PAK5- or YSK2-related gene product is secreted from the host cells, the exhausted nutrient medium can simply be collected and the product isolated therefrom.

The expressed MLK4-, PAK4-, PAK5- or YSK2-related gene product can be isolated or substantially purified from cell lysates or culture medium, as appropriate, using standard methods, including but not limited to any combination of the following methods: ammonium sulfate precipitation, size fractionation, ion exchange chromatography, HPLC, density centrifugation, and affinity chromatography. Where the expressed MLK4-, PAK4-, PAK5- or YSK2-related gene products exhibit biological activity, increasing purity of the preparation can be monitored at each step of the purification procedure by use of an appropriate assay. Whether or not the expressed MLK4-, PAK4-, PAK5- or YSK2-related gene products exhibit biological activity, each can be detected as based, e.g., on size, or reactivity with an antibody otherwise specific for MLK4, PAK4, PAK5 or YSK2, or by the presence of a fusion tag.

The present invention thus provides a substantially purified or isolated polypeptide encoded by a polynucleotde molecule of the present invention. In a specific though non-limiting embodiment, the polypeptide is a human MLK4 gene product, or a portion thereof, comprising the amino acid sequence of SEQ ID NO:2. In another specific though non-limiting embodiment, the polypeptide is a human PAK4 gene product, or a portion thereof, comprising the amino acid sequence of SEQ ID NO:4. In still another specific though non-limiting embodiment, the polypeptide is a human PAK5 gene product, or a portion thereof, comprising the amino acid sequence of SEQ ID NO:6, 8 or 10. In another specific though non-limiting embodiment, the polypeptide is a human YSK-2 gene product, or a portion thereof, comprising the amino acid sequence of SEQ ID NO:13. The present invention further provides substantially purified or isolated polypeptides that are homologous to any of the MLK4, PAK4, PAK5 or YSK2 gene products of the present invention, as homologous polypeptides are defined above. The present invention further provides peptide fragments of the MLK4, PAK4, PAK5 or YSK2 gene products or homologous polypeptides of the present invention, as peptide fragments are defined above. The substantially purified or isolated polypeptides of the present invention are useful for a variety of purposes, such as, e.g., screening for compounds that interact with MLK4, PAK4, PAK5 or YSK2 proteins, and hence are candidates for compounds that affect MLK4, PAK4, PAK5 or YSK2 activity (including the events involved in signal transduction), and for raising antibodies directed against MLK4, PAK4, PAK5 or YSK2 gene product. Such compounds and antibodies can be used in therapeutic methods to treat or prevent UV damage to the skin.

As used herein, a polypeptide is "substantially purified" where the polypeptide constitutes the majority (i.e., at least about 50%) by weight of the material in a particular preparation. Also, as used herein, a polypeptide is "isolated" where the polypeptide constitutes at least about 90 wt % of the material in a particular preparation. Also, as used herein, a polynucleotide molecule is "isolated" where it constitutes at least about 90 wt % of the nucleic acid material in a particular preparation, or where it appears to be separated from all other polynucleotide molecules as determined, e.g., by gel electrophoresis techniques.

The present invention further provides a method of preparing a substantially purified or isolated MLK4 gene product, PAK4 gene product, PAK5 gene product, YSK2 gene product or peptide fragment of the present invention, comprising culturing a host cell transformed or transfected with a polynucleotide molecule or recombinant vector of the present invention, said recombinant vector comprising a polynucleotide molecule comprising a nucleotide sequence encoding the MLK4 gene product, PAK4 gene product, PAK5 gene product, YSK2 gene product or peptide fragment, respectively, of the present invention, wherein the nucleotide sequence is in operative association with one or more regulatory elements, under conditions conducive to the expression of the particular gene product, polypeptide, or peptide fragment, and recovering the expressed gene product, polypeptide, or peptide fragment, from the cell culture in a substantially purified or isolated form.

Once an MLK4, PAK4, PAK5 or YSK2 gene product of sufficient purity has been obtained, it can be characterized by standard methods, including by SDS-PAGE, size exclusion chromatography, amino acid sequence analysis, biological activity such an kinase activity, etc. For example, the amino acid sequence of the MLK4, PAK4, PAK5 or YSK2 gene product can be determined using standard peptide sequencing techniques. The MLK4. PAK4, PAK5 or YSK2 gene product can be further characterized using hydrophilicity analysis (see, e.g., Hopp and Woods, 1981, Proc. Natl. Acad. Sci. USA 78:3824), or analogous software algorithms, to identify hydrophobic and hydrophilic regions of the MLK4, PAK4, PAK5 or YSK2 gene product respectively. Structural analysis can be carried out to identify regions of the MLK4, PAK4, PAK5 or YSK2 gene product that assume specific secondary structures. Biophysical methods such as X-ray crystallography (Engstrom, 1974, Biochem. Exp. Biol. 11:7–13), computer modeling (Eletterick and Zoller (eds), 1986, in: Current Communications in Molecular Biology, Cold Spring Harbor Laboratory, Cold Spring Harbor, N.Y.), and nuclear magnetic resonance (NMR) can be used to map and study sites of interaction between the MLK4, PAK4, PAK5 or YSK2 gene products and their substrates. Information obtained from these studies can be used to select specific sites on the MLK4, PAK4, PAK5 or YSK2 gene products as potential targets for drug candidates that interact with, and alter the activity of, these gene products.

5.4. Antibodies

The present invention further provides polyclonal and monoclonal antibodies that bind to an MLK4 gene product, PAK4 gene product, PAK5 gene product, YSK2 gene product, or to an homologous polypeptide or peptide fragment, of the present invention. Such antibodies can be used as affinity reagents with which to purify a native MLK4, PAK4, PAK5 or YSK2 gene product, or to analyze the activity or biological function of the MLK4, PAK4, PAK5 or YSK2 gene product.

Antibodies can be raised against any of the MLK4-, PAK4-, PAK5- or YSK2-related polypeptides of the present invention. Various host animals, including but not limited to cows, horses, rabbits, goats, sheep, and mice, can be used according to known methods to produce anti-MLK4, anti-PAK4, anti-PAK5 or anti-YSK2-specific antibodies. Various adjuvants known in the art can be used to enhance antibody production.

Polyclonal antibodies can be obtained from immunized animals and tested for anti-MLK4, anti-PAK4, anti-PAK5 or anti-YSK2 specificity using standard techniques. Alternatively, monoclonal antibodies to an MLK4, PAK4, PAK5 or YSK2 polypeptide can be prepared using any technique that provides for the production of antibody molecules by continuous cell lines in culture. These include but are not limited to the hybridoma technique originally described by Kohler and Milstein (Nature, 1975, 256: 495–497); the human B-cell hybridoma technique (Kosbor, et al., 1983, Immunology Today 4:72; Cote, et al., 1983, Proc. Natl. Acad. Sci. USA 80: 2026–2030); and the EBV-hybridoma technique (Cole, et al., 1985, Monoclonal Antibodies and Cancer Therapy, Alan R. Liss, Inc., pp. 77–96). Alternatively, techniques described for the production of single chain antibodies (see, e.g., U.S. Pat. No. 4,946,778) can be adapted to produce MLK4-, PAK4-, PAK5- or YSK2-specific single chain antibodies. These publications are incorporated herein by reference.

Antibody fragments that contain specific binding sites for an MLK4, PAK4, PAK5 or YSK2 polypeptide are also encompassed within the present invention and can be generated by known techniques. Such fragments include but are not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab expression libraries can be constructed (Huse et al., 1989, Science 246: 1275–1281) to allow rapid identification of Fab fragments having the desired specificity to the MLK4, PAK4, PAK5 or YSK2 polypeptide.

Techniques for the production of monoclonal antibodies and antibody fragments are well-known in the art, and are additionally described, among other places, in Harlow and Lane, 1988, Antibodies: A Laboratory Manual, Cold Spring Harbor Laboratory; and in J. W. Goding, 1986, Monoclonal Antibodies: Principles and Practice, Academic Press, London. All of the above-cited publications are incorporated herein by reference.

5.5. Anti-sense Oligonucleotide and Ribozymes

Also within the scope of the present invention are oligonucleotide sequences that include anti-sense oligonucleotides, phosphorothioates and ribozymes that function to bind to, degrade and/or inhibit the translation of MLK4, PAK4, PAK5 or YSK2 mRNA.

Anti-sense oligonucleotides, including anti-sense RNA molecules and anti-sense DNA molecules, act to directly block the translation of mRNA by binding to targeted mRNA and preventing protein translation. For example, antisense oligonucleotides of at least about 15 bases and complementary to unique regions of the DNA sequence encoding an MLK4, PAK4, PAK5 or YSK2 polypeptide can be synthesized, e.g., by conventional phosphodiester techniques.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hammerhead motif ribozyme molecules that specifically and efficiently catalyze endonucleolytic cleavage of MLK4, PAK4, PAK5 or YSK2 mRNA sequences are also within the scope of the present invention.

Specific ribozyme cleavage sites within any potential RNA target are initially identified by scanning the target molecule for ribozyme cleavage sites that include the following sequences, GUA, GUU, and GUC. Once identified, short RNA sequences of between about 15 and 20 ribonucleotides corresponding to the region of the target gene containing the cleavage site can be evaluated for predicted structural features such as secondary structure that may render the oligonucleotide sequence unsuitable. The suitability of candidate targets can also be evaluated by testing their accessibility to hybridization with complementary oligonucleotides using, e.g., ribonuclease protection assays.

Both the anti-sense oligonucleotides and ribozymes of the present invention can be prepared by known methods. These include techniques for chemical synthesis such as, e.g., by solid phase phosphoamite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters.

Various modifications to the oligonucleotides of the present invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

5.6. Detection of JNKKK Gene Products, and Diagnostic and Therapeutic Uses

The MLK4, PAK4, PAK5 and YSK2 polynucleotide molecules, oligonucleotides, and polypeptides of the present invention, as well as antibodies of the present invention that recognize the MLK4, PAK4, PAK5 or YSK2 polypeptides, are useful in the diagnosis of diseases or conditions resulting from alteration in the expression of MLK4, PAK4, PAK5 or YSK2 gene products. Alteration in expression can be either an increase or decrease in transcription of the MLK4, PAK4, PAK5 or YSK2 gene, or an increase or decrease in translation of an MLK4, PAK4, PAK5 or YSK2 gene product. Alternatively, the presence of mutations, alleles, or polymorphisms in the MLK4, PAK4, PAK5 or YSK2 gene sequence can be correlated with diseases or conditions, including but not limited to increased or decreased susceptibility to skin damage caused by ultraviolet light or other stresses, or psoriasis.

Nucleic acid-based detection methods are well known in the art and include hybridization assays (e.g., Northern and Southern hybridizations, nuclease protection), polymerase chain reaction (PCR) assays, and ligation chain reaction (LCR) assays, or combinations of the above (e.g., in situ hybridization). Such assays make use of the MLK4, PAK4, PAK5 or YSK2 polynucleotides and oligonucleotides of the present invention, including complementary sequences, as described above. If analysis of an RNA gene product is desired, certain assays would typically include a reverse transcription step prior to amplification and/or hybridization, as known in the art. Such nucleic acid based techniques can be designed by those of ordinary skill in the art to assay the levels of MLK4, PAK4, PAK5 or YSK2 gene expression, or the presence or absence of particular mutations, alleles or polymorphisms.

Protein or polypeptide-based detection methods are also well known to those of ordinary skill and include, e.g., immunological assays such as Western blot, immunoprecipitation of labeled target, and ELISA assays. These assays use the antibodies of the present invention described above. Again, such assays can measure levels of MLK4, PAK4, PAK5 or YSK2 polypeptides expressed by a cell or organism, or the presence of mutants, alleles, or polymorphisms in the MLK4, PAK4, PAK5 or YSK2 polypeptides.

If an abnormal condition is associated with the over- or under-production of an MLK4, PAK4, PAK5 or YSK2 gene product, the polynucleotides and oligonucleotides of the invention can be useful in preventing, ameliorating or otherwise treating of the abnormal condition. For example, by introducing gene sequences into cells, gene therapy can be used to treat conditions in which the cells express inadequate levels of MLK4, PAK4, PAK5 or YSK2 gene product, or express abnormal or inactive MLK4, PAK4, PAK5 or YSK2 polypeptides. In some instances, abnormal conditions characterized by over-expression of MLK4, PAK4, PAK5 or YSK2 gene product can be prevented or treated using the gene therapy techniques described below. Specifically, gene therapy vectors can be designed to express anti-sense polynucleotides or ribozymes of the present invention as described above, thereby reducing the amount of MLK4, PAK4, PAK5 or YSK2 gene products that are effectively translated into polypeptide.

Expression vectors derived from viruses such as retroviruses, vaccinia virus, adeno-associated virus, herpes viruses, or papilloma virus can be used for delivery of recombinant MLK4, PAK4, PAK5 or YSK2 polynucleotides into the targeted cell population. Methods that are well known to those skilled in the art can be used to construct recombinant viral vectors containing an MLK4, PAK4, PAK5 or YSK2 polynucleotide. See, for example, the techniques described in Maniatis et al., 1989, Molecular Cloning A Laboratory Manual, Cold Spring Harbor Laboratory, N.Y.; and Ausubel et al., 1989, Current Protocols in Molecular Biology, Greene Publishing Associates and Wiley Interscience, N.Y. Alternatively, recombinant, non-viral vectors containing an MLK4, PAK4, PAK5 or YSK2 polynucleotide can be reconstituted into liposomes for delivery to target cells, or can be delivered as a naked polynucleotide, such as, e.g., in a "DNA Vaccine," to name just a few examples.

5.7. Drug Screening Applications

MLK4, PAK4, PAK5 and YSK2 gene products, including polynucleotides, oligonucleotides and polypeptides, can be used in screening assays to identify compounds that specifically bind to MLK4, PAK4, PAK5 or YSK2 gene products and thus have potential use as agonists or antagonists of MLK4, PAK4, PAK5 or YSK2 polypeptides, respectively. In a particular preferred use, the polynucleotides and polypeptides of the invention are useful to screen for compounds that affect the kinase activities of MLK4, PAK4, PAK5 or YSK2 polypeptides.

The invention thus provides assays to detect molecules that specifically bind to MLK4, PAK4, PAK5 or YSK2 polypeptides. For example, recombinant cells expressing an MLK4, PAK4, PAK5 or YSK2 polynucleotide can be used to recombinantly produce an MLK4, PAK4, PAK5 or YSK2 polypeptide, respectively, and to screen for molecules that bind to an MLK4, PAK4, PAK5 or YSK2 polypeptide, respectively. Methods that can be used to carry out the foregoing are commonly known in the art.

Diversity libraries, such as random or combinatorial peptide or non-peptide libraries can be screened for molecules that specifically bind to an MLK4, PAK4, PAK5 or YSK2 polypeptide. Many libraries are known in the art that can be used such as, e.g., chemically synthesized libraries, recombinant (e.g., phage display) libraries, and in vitro translation-based libraries.

Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242, dated Oct. 14, 1993; and Brenner and Lerner, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, R. B. et al., 1992, J. Mol. Biol. 227:711–718; Lenstra, 1992, J. Immunol. Meth. 152:149–157; Kay et al., 1993, Gene 128:59–65; and PCT Publication No. WO 94/18318, dated Aug. 18, 1994.

In vitro translation-based libraries include but are not limited to those described in PCT Publication No. WO 91/05058, dated Apr. 18, 1991; and Mattheakis et al., 1994, Proc. Natl. Acad. Sci. USA 91:9022–9026.

In one example, non-peptide libraries, such as a benzodiazepine library (see e.g., Bunin et al., 1994, Proc. Natl. Acad. Sci. USA 91:4708–4712), can be screened. Peptoid libraries, such as that described by Simon et al., 1992, Proc. Natl. Acad. Sci. USA 89:9367–9371, can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

Screening the libraries can be accomplished by any of a variety of commonly known methods. See, for example, the following references, which disclose screening of peptide libraries: Parmley and Smith, 1989, Adv. Exp. Med. Biol. 251:215–218; Scott and Smith, 1990, Science 249:386–390; Fowlkes et al., 1992, BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar and Pabo, 1993, Science 263:671–673; and PCT Publication No. WO 94/18318.

In a specific embodiment, screening can be carried out by contacting the library members with an MLK4, PAK4, PAK5 or YSK2 polypeptide immobilized on a solid phase and harvesting those library members that bind to the polypeptide. Examples of such screening methods, termed "panning" techniques, are described by way of example in Parmley and Smith, 1988, Gene 73:305–318; Fowlkes et al., 1992, BioTechniques 13:422–427; PCT Publication No. WO 94/18318; and in other references cited hereinabove.

In another embodiment, the two-hybrid system for selecting interacting proteins in yeast (Fields and Song, 1989, Nature 340:245–246; Chien et al., 1991, Proc. Natl. Acad. Sci. USA 88:9578–9582) can be used to identify molecules that specifically bind to an MLK4, PAK4, PAK5 or YSK2 polypeptide within a cell.

In another aspect of the invention, methods for screening candidate compounds for drugs are provided. Such drugs can be used to reduce ultraviolet light-induced damage, inflammation and psoriasis, and enhance wound healing in a subject. The subject is an animal, typically a mammal, preferably a human.

For example, one can screen for compounds that affect the expression of an MLK4, PAK4, PAK5 or YSK2 gene product of the present invention by: (a) applying a test compound to a test sample; (b) determining the expression of at least one MLK4, PAK4, PAK5 or YSK2 gene product in the test sample; and (c) comparing the expression of the gene in the test sample with that in a reference sample. A specific change in the cellular level of the gene product in the test sample as compared to the reference sample indicates that the compound affects the cellular level of gene product from a JNKKK gene. By the term "a specific change in the cellular level of the gene product" is meant that the change in level occurs without alteration of overall transcription or translation levels in the cell (depending upon the gene product assayed). For example, when mRNA is measured, a compound that causes a "specific change" is not a compound that is a general transcriptional repressor. Similarly, for example, when protein levels are assayed, a compound that causes a "specific change" is not a general translational repressor. One can determine whether global effects on transcription or translation occur in the presence of a test compound by assaying for a control housekeeping gene product (e.g., glucose-6-phosphate dehydrogenase gene product or the actin gene product, to name just two examples).

One can also assay the effect of a test compound on the expression or cellular response of the MLK4, PAK4, PAK5 or YSK2 gene or polypeptide in the presence of, or in response to, a stress event. The stress event applied to the cells can be exposure to ultraviolet radiation. Preferred ultraviolet radiation can be UV-A with a wavelength in the range of 320–400 nm, or UV-B with a wavelength in the range of 280–320 nm, or UV-C with a wavelength in the range of 200–280 nm. Other types of stress events applied to the sample for screening purposes can be exposure to inflammatory cytokines such as TNF-α, IL-1, interferons, FGFs or PDGF. Still other types of stress events are heat shock, osmotic shock, exposure to toxic chemicals such as arsenic, disruption of the permeability barrier (e.g., with solvents), etc.

In one preferred embodiment, the method of drug screening comprises: (a) applying a test compound to a test sample; (b) exposing the test sample and a reference sample to a stress event; (c) determining the expression of at least one gene product in the test sample, wherein the transcript of the gene product comprises a sequence selected from the group consisting of SEQ ID NOS: 1, 3, 5, 7, 9, 11 and 12; and (d) determining the effectiveness of the test compound in blocking or otherwise modulating the cellular response to the stress event by comparing the expression of the gene product in the test sample with that in the reference sample. If the test compound significantly reduces the expression of the transcript in response to the stress event, the test compound is identified as a drug candidate that may be potentially effective in blocking the cellular response to the stress event. The expression of the MLK4, PAK4, PAK5 or YSK2 gene product can be determined using any of the methods described above. The most preferred gene products for use in this assay are the PAK5 and YSK2 gene products.

In another preferred embodiment, the method of drug screening entails: (a) applying a test compound to a test sample; (b) applying a stress event to the test sample; and (c) determining the amount of an MLK4, PAK4, PAK5 or YSK2 polypeptide in the test sample and in a reference sample, wherein the MLK4, PAK4, PAK5 or YSK2 polypeptide comprises an amino acid sequence selected from the group consisting of: SEQ ID NOS: 2, 4, 6, 8, 10 and 13; wherein a reduction in the amount of the MLK4, PAK4, PAK5 or YSK2 polypeptide in the test sample as compared to that in the reference sample indicates that the test compound is identified as a drug candidate that can potentially block the stress response.

Still another aspect of the invention is a method of screening for compounds that affect the activity of an MLK4, PAK4, PAK5 or YSK2 polypeptide. One can apply a test compound to a test sample and determine the activity of the MLK4, PAK4, PAK5 or YSK2 polypeptide in the test sample compared to that in a reference sample. A test compound that alters the MLK4, PAK4, PAK5 or YSK2 polypeptide activity in the test sample as compared to the reference sample is identified as a drug candidate that can potentially affect the activity of the MLK4, PAK4, PAK5 or YSK2 polypeptide. Each of the full-length MLK4, PAK4, PAK5 and YSK2 polypeptides is a kinase; thus, the activities of these polypeptides include kinase activity and binding to ATP and its analogs. Other activities include the ability to interact with activators that activate MLK4, PAK4, PAK5 or YSK2 polypeptide kinase activity, interaction with downstream target proteins, and interaction with inhibitors via the amino-terminal regulatory domain.

In another preferred embodiment, the activity of MLK4, PAK4, PAK5 or YSK2 polypeptides, such as kinase activity, binding to ATP and its analogs, or activation of downstream target protein, can be assayed in the test and reference samples in response to application of a stress event, and compared, to predict the effectiveness of the drug candidate. If the drug candidate prevents the induction of the function of the MLK4, PAK4, PAK5 or YSK2 polypeptide by a particular stress event, such as ultraviolet radiation, the drug candidate can be effective at blocking the stress response.

In some preferred embodiments, the test and reference samples are cultured cells, tissues or organs. In other preferred embodiments, the test and reference samples are live animals. In a particularly preferred embodiment, a small biopsy of human skin (e.g., about 5 mm$^3$) is placed in culture and treated with, e.g., ultraviolet radiation, one or more growth factors, cytokines, drugs, hormones or vitamins. After a defined period of time (typically 24–48 hours when the treatment is ultraviolet radiation), the biopsy is tested for expression of the MLK4, PAK4, PAK5 or YSK2 gene product, or for activity of the MLK4, PAK4, PAK5 or YSK2 polypeptide.

The invention having been described, the following examples are offered by way of illustration and not limitation.

6. EXAMPLE

Cloning of the YSK2, MLK4, PAK4 and PAK5 cDNAs

This example illustrates the methods used to clone the novel JNKKKs of the invention.

6.1. Materials and Methods

Normal human foreskin epidermal keratinocytes were a generous gift from Dr. M. Simon of the State University of New York at Stony Brook. The cultures were initiated using 3T3 feeder layers and then frozen in liquid nitrogen until used. Once thawed, the keratinocytes were grown without feeder cells in defined serum-free keratinocyte growth medium (KGM), supplemented with bovine pituitary extract epidermal growth factor, insulin, thyroid hormone and hydrocortisone (keratinocyte-SFM, GIBCO).

Messenger RNA from the keratinocytes was used for reverse transcription polymerase chain reaction (RT-PCR) amplification with an RT-PCR kit (Promega Corp., Madison, Wis.). Primers corresponding to regions of homology between the kinase domains of JNKKs or JNKKKs were designed to amplify a 150 bp PCR products from keratinocyte mRNA using RT-PCR. The primers contain the following sequences that correspond to the regions of the kinase domain.

Forward: 5'-ATGCA(CA)CANGA(CT)AT(ACT)AA(AG)3' (SEQ ID NO:14)

Reverse: 5'-GCNAC(CT)TCNGGNGCCATCCA-3' (SEQ ID NO:15)

The actual primers used for RT-PCR also contained cloning sites. Their sequences are as follows:

Forward: 5'-CCCGAATTCATGCA(CA)CANGA(CT)AT(ACT)AA(AG)-3' (SEQ ID NO:16)

Reverse: 5'-CCCGAATTCGCNAC(CT)TCNGGNGCCATCCA-3' (SEQ ID NO: 17)

The PCR products were sub-cloned and sequenced.

6.2. Results

Among the seventy different clones sequenced, ten different JNKKKs were identified, four of which appeared to be novel. An amino acid sequence comparison against the protein databases in the European Molecular Biology Network (available at HYPERLINK http://www.expasy.ch; http://www.expasy.ch; http://www.ch.embnet.org) with other JNKKKs revealed that the four novel JNKKKs exhibited some degree of homology to various known JNKKKs from several different families. One JNKKK clone was 91% identical at positions 12–131 to a 134 base region of the murine YSK2 gene sequence (corresponding to positions 503–384 of emb: U49949, Osada et al., 1997, Oncogene 14:2047–2057); hence, this clone was designated as the human keratinocyte YSK2 (SEQ ID NO:12). Additionally, two human expressed sequence tags (ESTs) were related to the human keratinocyte YSK2. Specifically, Human EST emb:AA557573 (NCI-CGAP, "National Cancer Institute, Cancer Genome Anatomy Project (CGAP), Tumor Gene Index http:/twww.ncbi.nlm.nih.gov/ncicgap," Unpublished.) showed a 96% identity with the human YSK2 gene sequence (SEQ ID NO:12) in a 137 bp region corresponding to positions 6–142 of SEQ ID NO:12 and positions 32–168 of emb:AA557573. Human EST emb:AA578088 (NCI-CGAP, "National Cancer Institute, Cancer Genome Anatomy Project (CGAP), Tumor Gene Index http://www.ncbi.nim.nih.gov/ncicgap," Unpublished.) also showed a 96% identity with the SEQ ID NO:12 in a 136 bp region corresponding to positions 6–141 of SEQ ID NO:12 and positions 35–170 of emb:AA578088.

Another JNKKK clone, designated MLK4 (SEQ ID NO:1), was 50% to 78% identical to members of the MLK family of JNKKKs. Finally, two JNKKK clones, designated PAK4 (SEQ ID NO:3) and PAK5 (SEQ ID NO:5), showed similar identity to members of the PAK family of JNKKKs. However, no homolog sequences could be found in the European Molecular Biology Network protein database for either MLK4 or PAK5. Although initial sequence searches of PAK4 indicated it was a new member of the PAK gene family, during the course of this work, the complete sequence of human PAK4 was published (Abo et al., 1998, EMBO J 22:6527–6540).

The relative abundance of the different identified JNKKKs is shown below in TABLE 1 below.

TABLE 1

ABUNDANCE OF DIFFERENT JNKKKS

| Kinase | Number of Isolates |
| --- | --- |
| BPAG1* | 1 |
| GCK | 3 |
| LIMK | 1 |
| MEKK3 | 4 |
| MLK4 | 2 |
| NiK | 94 |
| PAK1 | 40 |
| PAK2 | 31 |
| PAK4 | 69 |
| PAK5 | 59 |
| YSK1 | 1 |
| Ysk2 | 51 |
| Total | 356 |

*LIMK is a protein kinase, related to, but not a member of, the JNKKK family. Frangiskakis et al., 1996, Cell 86:59–69. BPAG1 is an abundant protein in basal keratinocytes. Its mRNA contains two segments recognized by the 8 bases at the 3' termini of our oligonucleotides.

The RT-PCR products (SEQ ID NOS:1, 3, 5, 12) of the MLK4, PAK4, PAK5 and YSK2 mRNAs were used as probes for Northern Hybridization to mRNAs from heart, brain, placenta, lung, liver, skeletal muscle, kidney and pancreas. FIG. 2 shows that the expression of the PAK4 gene is ubiquitous among the organs tested. However, the PAK5 gene is strongly expressed in keratinocytes and in the brain, but not expressed, or only weakly expressed, in placenta, lung, liver, skeletal muscle, kidney and pancreas. The MLK4 gene is expressed in keratinocytes, kidney and pancreas, but not in the brain, placenta, lung, liver, and skeletal muscle. The size of the transcripts of PAK4, PAK5 and MLK4 are 3.4, 4.4 and 4.8 kb, respectively.

7. EXAMPLE

Genomic Sequence of the PAK5 Gene

Oligonucleotides 5'-GAGTGACTCCATCCTGC-3' (SEQ ID NO: 18) and 5'-GTAGGGGGTTCCCACCA-3' (SEQ ID NO: 19) were used to identify a genomic clone from a commercially available P1 human library (Genome Systems, Inc., St. Louis, Mo.) that contained the PAK5 gene. The P1 genomic clone was partially sequenced, and additional coding sequence deduced. The polynucleotide sequence, with deduced exons indicated, is presented as SEQ ID NO:7. SEQ ID NO:8 presents the deduced amino acid sequence from the partial genomic sequence. A partial schematic structure of the PAK5 gene is depicted in FIG. 1. A PLC-2 gene was found to be linked to the PAK5 gene in the P1 clone. The PLC-2 gene has been mapped to chromosome 15; thus, the PAK5 gene also must reside on chromosome 15.

The deduced amino acid sequence of the PAK5 protein (SEQ ID NO:8) is very similar to that of PAK4 (SEQ ID NO:4), especially in the kinase domain (amino acid residues 93 to 311 in SEQ ID NO:8). The kinase domains of any of the JNKKKs of the present invention have utility as enzymatically active domains to phosphorylate substrates. The sequence of the PAK5 kinase domain contains a conserved lysine (K) residue that is essential for ATP binding (amino acid residue 120 in SEQ ID NO:8). By analogy with PAK4, mutations that change this lysine residue in PAK5 to alanine or methionine residues will abolish PAK5 enzymatic activity, while mutations that change the lysine residue to a glutamine will make a full length PAK5 protein constitutively active. Less homology between PAK4 and PAK5 is observed outside of the kinase domain. The 21 residue carboxy terminal extension of PAK5 is 4 amino acids longer than that of PAK4. Additionally, the available amino terminal sequences of the PAK5 protein bear no similarity to any known protein other than PAK4. Thus, both the carboxy terminal and the amino terminal regions of the PAK5 protein will be particularly useful in generating antibodies that immunospecifically recognize PAK5.

The ORF of the complete human cDNA sequence of PAK5 is presented in SEQ ID NO:9 from nt 199–2244. The complete DNA sequence for the human PAK5 gene is presented in SEQ ID NO:10, with the ORF from nt 6125–17433.

8. EXAMPLE

Ultraviolet Radiation-induced Expression of YSK2 and PAK5 mRNA

In this example, the effect of various wavelengths of ultraviolet radiation on the expression of the novel JNKKKs was investigated. The effects of both UV-C light (short wavelength ultraviolet radiation of 220 to 290 nm) and UV-A light (long wavelength ultraviolet radiation of 320 to 400 nm) were separately analyzed.

Keratinocytes were grown as described in Section 6.1, above. The cells were expanded through two 1:4 passages before illumination with 3–10 mJ/cm2 of UV-C light or 1–5 J/cm2 of UV-A light. Cells were harvested 6 or 24 hours after exposure. PolyA mRNA was purified from the cells using kits from Qiagen.

FIG. 3A shows that the YSK2 gene is induced by UV-C light. Keratinocytes were exposed to 10 mJ/cm2 of UV-C light. Messenger RNAs from control and UV-C light-treated cells were separated by electrophoresis and transferred to a membrane by Northern blotting. The membrane was then hybridized using the 190 bp YSK2 RT-PCR product labeled with $^{32}$P-dNTPs as the probe. As FIG. 3A shows, the expression of the YSK2 gene in keratinocytes was greatly enhanced by UV-C light exposure.

FIG. 3B shows that the PAK5 gene is induced by UV-A light treatment. Human keratinocytes were exposed to UV-A light (5 mJ/cm2), harvested, and mRNA prepared from the cells. The levels of PAK4 and PAK5 mRNA in treated and untreated cells were compared using differential display. Liang and Pardee, 1992, Science 257:967–71. Amplification was performed using primer SEQ ID NOS:14 and 15, or SEQ ID NO:16 and 17, above. The resulting amplified DNA was then digested with restriction enzyme Taql to reveal specifically the PAK4 and the PAK5 DNAs. The results demonstrate that PAK5 is induced by ultraviolet radiation.

Differential display experiments (FIGS. 3A and 3B) show that expression of both YSK2 and PAK5 genes are induced by ultraviolet radiation. However, induction of the two genes is dependent upon the wavelength of the ultraviolet radiation. YSK2 gene expression is induced by UV-C, which is the short wavelength ultraviolet radiation (220 to 290 nm). In contrast, the PAK5 gene expression is induced by UV-A, which is the long wavelength ultraviolet radiation (320 to 400 nm). The induction of YSK2 and PAK5 gene expression by ultraviolet radiation suggests that the products of the two genes are involved in the signal transduction cascade that transduces extracellular ultraviolet radiation (or other stress signals). Although MLK4 and PAK4 mRNA gene expression were not induced by ultraviolet radiation in these experiments, this fact cannot rule out a role in the keratinocyte response to light or other stresses. These gene products can be involved in the early cellular events in response to stress prior to any changes in gene expression.

The foregoing written specification is sufficient to enable one skilled in the art to practice the invention. Indeed, various modifications of the above-described means for carrying out the invention which are obvious to those skilled in the field of molecular biology, medicine or related fields are intended to be within the scope of the following claims.

All references referred to herein above are incorporated herein by reference in their entirety.

What is claimed is:

1. An isolated polynucleotide molecule comprising a nucleotide sequence encoding an MLK4 gene product from a human, wherein the MLK4 gene product comprises the amino acid sequence of SEQ ID NO:2.

2. The isolated polynucleotide sequence of claim 1 comprising the nucleotide sequence of SEQ ID NO:1.

3. An isolated polynucleotide molecule that comprises a nucleotide sequence that is about 90% homologous to SEQ ID NO:1, wherein the isolated polynucleotide molecule encodes a protein that has a kinase activity of an MLK4 gene product.

4. An isolated polynucleotide molecule that comprises a nucleotide sequence that is about 90% homologous to a nucleotide sequence that encodes a polypeptide comprising SEQ ID NO:2, wherein the isolated polynucleotide molecule encodes a protein that has a kinase activity of an MLK4 gene product.

5. An isolated polynucleotide molecule that specifically hybridizes under highly stringent conditions to a complement of a sequence comprising SEQ ID NO:1, wherein the nucleic add encodes a protein that has a kinase activity of an MLK4 gene product.

6. An isolated polynucleotide molecule that specifically hybridizes under highly stringent conditions to a complement of a polynucleotide sequence comprising a nucleotide sequence that encodes a polypeptide comprising SEQ ID NO:2, wherein the nucleic add molecule encodes a protein that has a kinase activity of an MLK4 gene product.

7. A process for producing an isolated polynucleotide, comprising hybridizing SEQ ID NO:1 to genomic DNA under highly stringent conditions and isolating the DNA polynucleotide detected with SEQ ID NO:1.

8. The isolated DNA polynucleotide prepared according to the process of claim 7.

9. An isolated polynucleotide molecule that is the complement of the polynucleotide molecule of claim 1, 2, 3, 4, 5, 6 or 8.

10. A recombinant vector comprising the polynucleotide molecule of claim 1, 2, 3, 4, 5, 6, or 8.

11. A transformed host cell comprising the recombinant vector of claim 10.

12. A method of preparing a substantially purified or isolated polypeptide encoded by the recombinant vector of claim 10, comprising culturing host cells transformed with the recombinant vector under conditions conducive to the expression of the polypeptide, and recovering in substantially purified or isolated form the polypeptide from the cell culture.

* * * * *

UNITED STATES PATENT AND TRADEMARK OFFICE
CERTIFICATE OF CORRECTION

PATENT NO. : 6,861,239 B1
DATED : February 8, 2005
INVENTOR(S) : Blumenberg et al.

It is certified that error appears in the above-identified patent and that said Letters Patent is hereby corrected as shown below:

Column 6,
Line 22, please replace "for the. YSK2" with -- for the YSK2 --

Column 12,
Line 24, please replace "PAKS-related" with -- PAK5-related --

Column 13,
Line 22, please replace "and Is useful" with -- and is useful --

Column 22,
Line 14, please replace "The MLK4 PAK4," with -- The MLK4, PAK4, --

Column 27,
Line 58, please replace "PAK4, PAKS or YSK2" with -- PAK4, PAK5 or YSK2 --

Column 28,
Line 2, please replace "a lest compound" with -- a test compound --

Column 70,
Line 49, please replace "nucleic add" with -- isolated polynucleotide molecule --
Line 55, please replace "nucleic add" with -- isolated polynucleotide --
Line 57, please replace "isolated polynucleotide" with -- isolated DNA polynucleotide --

Signed and Sealed this

Thirty-first Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,861,239 B1
DATED : February 8, 2005
INVENTOR(S) : Blumenberg et al.

It is certified that error appears in the above-identified patent and that said Letters Patent is hereby corrected as shown below:

Title page,
Item [56], References Cited, U.S. PATENT DOCUMENTS, please add the following:
-- 5,908,836   06/1999   Bar-Shalom.............. 514/53
   5,916,880   06/1999   Bar-Shalom.............. 514/53
   5,939,457   08/1999   Miser..................... 514/557
   5,939,082   08/1999   Oblong................... 424/401
   5,962,534   10/1999   Gudas..................... 514/690 --.

OTHER PUBLICATIONS, please add the following:

--Zhuang et al., "Molecular Mechanism of Ultraviolet-Induced Keratinocyte Apoptosis," Journal of Interferon and Cytokine Research, vol. 20, 2000, pp 445-454.

Assefa et al., "Differential Stimulation of ERK and JNK Activities by Ultraviolet B Irradiation and Epidermal Growth Factor in Human Keratinocytes," vol. 108, no. 6, June 1997, pp 886-890.

Kligman et al., "The Nature of Photoaging: Its Prevention and Repair," Photodermatology, vol. 3, 1986, pp 215-227.

Lavker et al., "Aged Skin: A Study by Light, Transmission Electron, and Scanning Electron Microscopy," The Journal of Investigative Dermatology, vol. 88, no. 3, 1987, 44s-51s.

Lavker et al., "Structural Alterations in Exposed and Unexposed Aged Skin," The Journal of Investigative Dermatology, vol. 73, no. 1, pp 59-66.

Gilchrest, "Skin and Aging Process," 1984, CRC Press, Inc.

Deriijard et al., "JNK1: A Protein Kinase Stimulated by UV Light and Ha-Ras that Binds and Phosphorylates the c-Jun Activation Domain," Cell, vol. 76, March 25, 1994, pp 1025-1037.

Kyriakis et al., "The Stress-Activated Protein Kinase Subfamily of c-Jun Kinases," Nature, vol. 369, May 12, 1994, pp 156-160.

Rosette et al., "Ultraviolet Light and Osmotic Stress: Activation of the JNK Cascade Through Multiple Growth Factor and Cytokine Receptors," Science, vol. 274, Issue 5290, Nov. 15, 1996, pp 1194-1197.

Cavigelli et al., "The Tumor Promoter Arsenite Stimulates AP-1 Activity by Inhibiting a JNK Phosphatase," EMBO J. vol. 15, no. 22, 1996, pp 6269-6279.

Kallunki et al., "c-Jun Can Recruit JNK to Phosphorylate Dimerization Partners via Specific Docking Interactions," Cell, vol. 87, November 29, 1996, pp 929-939.

Fanger et al., "MEKKs, GCKs, MLKs, PAKs, TAKs and Tpls: Upstream Regulators of the c-Jun Amino Terminal Kinases," Oncogenes and Cell Proliferation, pp 67-74.

Devary et al., "NFkB Activation by Ultraviolet Light Not Dependent on a Nuclear Signal," Science, vo. 261, September 10, 1993, pp 1441-1445.

Simon et al., "UVB Light Induces NFkB Activity Independently From Chromosomal DNA Damage in Cell-Free Cytosolic Extracts," The Society for Investigative Dermatology, vol. 102, no. 4, April 1994, pp 422-427.

Li et al., "Ionizing Radiation and Short Wavelength UV Activate NFkB Through Two Distinct Mechanisms," Proc. Natl. Acad. Sci. USA, vol. 95, Issue 22, October 27, 1998, pp 13012-13017.

Garmyn et al., "Immediate and Delayed Molecular Response of Human Keratinocytes to Solar-Stimulated Irradiation," Laboratory Investigation, vol. 65, no. 4, 1991, pp 471-478.

Abts et al., "Analysis of UVB-modulated Gene Expression in Human Keratinocytes by mRNA Differential Display Polymerase Chain Reaction," Photochemistry and Photobiology, vol. 66, no. 3, 1997, pp 363-367.

Eller, "Photodamage," Blackwell, 1995, pp 26-56.

UNITED STATES PATENT AND TRADEMARK OFFICE
CERTIFICATE OF CORRECTION

PATENT NO. : 6,861,239 B1
DATED : February 8, 2005
INVENTOR(S) : Blumenberg et al.

It is certified that error appears in the above-identified patent and that said Letters Patent is hereby corrected as shown below:

Title page (cont'd),

Lockhart et al., "Expression Monitoring by Hybridization to High-Density Oligonucleotide Arrays," Nature Biotechnology, vol. 14, December 1996, pp 1675-1680.
Johnston et al., "Gene Chips: Array of Hope for Understanding Gene Regulation," Current Biology, vol. 8, 1998, pp R171-R174.
Scherf et al., "A Gene Expression Database for the Molecular Pharmacology of Cancer," Nature Genetics, vol. 24, March 2000, pp 236-244.
Ross et al., "Systematic Variation in Gene Expression Patterns in Human Cancer Cell Lines," Nature Genetics, vol. 24, March 2000, pp 227-235.

Welford et al., "Detection of Differentially Expressed Genes in Primary Tumor Tissues Using Representational Difference Analysis Coupled to Microarray Hybridization," Nucleic Acids Research, vo. 26, no. 12, 1998, pp 3059-3065.
Alon et al., "Broad Patterns of Gene Expression Revealed by Clustering Analysis of Tumor and Normal Colon Tissues Probed by Oligonucleotide Arrays," Proc. Natl. Acad. Sci. USA, vol. 96, issue 12, June 8, 1999, pp 6745-6750.
Golub et al., "Molecular Classification of Cancer: Class Discovery and Class Prediction by Gene Expression Monitoring," Science, vol. 286, October 15, 1999, pp 531-537.
Fambrough et al., "Diverse Signaling Pathways Activated by Growth Factor Receptors Induce Broadly Overlapping, Rather Than Independent Sets of Genes," Cell vol. 97, June 11, 1999, pp 727-741.
Galitski et al., "Ploidy Regulation of Gene Expression," Science, vol. 285, July 9, 1999, pp 251-253.
Lee et al., "Gene Expresson Profile of Aging and its Retardation by Caloric Restriction," Science, vol. 285, August 27, 1999, pp. 1390-1392.
Ly et al., "Mitotic Misregulation and Human Aging," Science, vol. 287, March 31, 2000, pp 2486-2492.
Harkin et al., "Induction of GADD45 and JNK/SAPK-Dependent Apoptosis Following Inducible Expression of BRCA1," Cell, vol. 97, May 28, 1999, pp 575-586.
Jelinsky et al., "Global Response of Saccharomyces cerevisiae to an Alkylating Agent," Proc. Natl. Acad. Sci. USA. vol. 96, issue 4, February 16, 1999, pp 1486-1491.
Kligman et al., "Photoaging," Fitzpatrick's Dermatology in Medicine, 1999, McGraw Hill, pp 1717-1721.
Bennett et al., Geneseq Database, Accession No. AAT03098, February 1996.--

Signed and Sealed this

Thirtieth Day of August, 2005

JON W. DUDAS
*Director of the United States Patent and Trademark Office*

SEQUENCE LISTING

```
<160> NUMBER OF SEQ ID NOS: 19

<210> SEQ ID NO 1
<211> LENGTH: 164
<212> TYPE: DNA
<213> ORGANISM: Homo sapiens
<220> FEATURE:
<221> NAME/KEY: CDS
<222> LOCATION: (2)...(163)

<400> SEQUENCE: 1 g cac cgg gac atc aag gca gga aat att ttg cta ctt gag aag ata gaa        49
  His Arg Asp Ile Lys Ala Gly Asn Ile Leu Leu Leu Glu Lys Ile Glu
    1               5                  10                  15 cat gat gac atc tgc aat aaa act ttg aag att aca gat ttt ggg ttg        97
His Asp Asp Ile Cys Asn Lys Thr Leu Lys Ile Thr Asp Phe Gly Leu
            20                  25                  30 gcg agg gaa tgg cac agg acc acc aaa atg agc aca gca ggc acc tat       145
Ala Arg Glu Trp His Arg Thr Thr Lys Met Ser Thr Ala Gly Thr Tyr
        35                  40                  45 gcc tgg atg gcc cca gaa g                                              164
Ala Trp Met Ala Pro Glu
```

```
<210> SEQ ID NO 2
<211> LENGTH: 54
<212> TYPE: PRT
<213> ORGANISM: Homo sapiens

<400> SEQUENCE: 2

His Arg Asp Ile Lys Ala Gly Asn Ile Leu Leu Glu Lys Ile Glu
 1               5                  10                  15

His Asp Asp Ile Cys Asn Lys Thr Leu Lys Ile Thr Asp Phe Gly Leu
            20                  25                  30

Ala Arg Glu Trp His Arg Thr Thr Lys Met Ser Thr Ala Gly Thr Tyr
        35                  40                  45

Ala Trp Met Ala Pro Glu
    50

<210> SEQ ID NO 3
<211> LENGTH: 145
<212> TYPE: DNA
<213> ORGANISM: Homo sapiens
<220> FEATURE:
<221> NAME/KEY: CDS
<222> LOCATION: (2)...(145)

<400> SEQUENCE: 3 a cat cgg gac atc aag agc gac tcg atc ctg ctg acc cat gat ggc agg      49
  His Arg Asp Ile Lys Ser Asp Ser Ile Leu Leu Thr His Asp Gly Arg
   1               5                  10                  15 gtg aag ctg tca gac ttt ggg ttc tgc gcc cag gtg agc aag gaa gtg        97
Val Lys Leu Ser Asp Phe Gly Phe Cys Ala Gln Val Ser Lys Glu Val
            20                  25                  30 ccc cga agg aag tcg ctg gtc ggc acg ccc tac tgg atg gcc cca gag        145
Pro Arg Arg Lys Ser Leu Val Gly Thr Pro Tyr Trp Met Ala Pro Glu
        35                  40                  45

<210> SEQ ID NO 4
<211> LENGTH: 48
<212> TYPE: PRT
<213> ORGANISM: Homo sapiens

<400> SEQUENCE: 4

His Arg Asp Ile Lys Ser Asp Ser Ile Leu Leu Thr His Asp Gly Arg
 1               5                  10                  15

Val Lys Leu Ser Asp Phe Gly Phe Cys Ala Gln Val Ser Lys Glu Val
            20                  25                  30

Pro Arg Arg Lys Ser Leu Val Gly Thr Pro Tyr Trp Met Ala Pro Glu
        35                  40                  45

<210> SEQ ID NO 5
<211> LENGTH: 146
<212> TYPE: DNA
<213> ORGANISM: Homo sapiens
<220> FEATURE:
<221> NAME/KEY: CDS
<222> LOCATION: (2)...(145)

<400> SEQUENCE: 5 t cac agg gac atc aag agt gac tcc atc ctg ctg acc ctc gat ggc agg      49
  His Arg Asp Ile Lys Ser Asp Ser Ile Leu Leu Thr Leu Asp Gly Arg
   1               5                  10                  15 gtg aag ctc tcg gac ttc gga ttc tgt gct cag atc agc aaa gac gtc        97
Val Lys Leu Ser Asp Phe Gly Phe Cys Ala Gln Ile Ser Lys Asp Val
```

```
                    20                  25                  30
cct aag agg aag tcc ctg gtg gga acc ccc tac tgg atg gcg ccc gag      145
Pro Lys Arg Lys Ser Leu Val Gly Thr Pro Tyr Trp Met Ala Pro Glu
         35                  40                  45 g                                                                    146

<210> SEQ ID NO 6
<211> LENGTH: 48
<212> TYPE: PRT
<213> ORGANISM: Homo sapiens

<400> SEQUENCE: 6

His Arg Asp Ile Lys Ser Asp Ser Ile Leu Leu Thr Leu Asp Gly Arg
  1               5                  10                  15

Val Lys Leu Ser Asp Phe Gly Phe Cys Ala Gln Ile Ser Lys Asp Val
                 20                  25                  30

Pro Lys Arg Lys Ser Leu Val Gly Thr Pro Tyr Trp Met Ala Pro Glu
         35                  40                  45

<210> SEQ ID NO 7
<211> LENGTH: 3627
<212> TYPE: DNA
<213> ORGANISM: Homo sapiens
<220> FEATURE:
<221> NAME/KEY: CDS
<222> LOCATION: (868)..(1275)
<221> NAME/KEY: CDS
<222> LOCATION: (1420)..(1553)
<221> NAME/KEY: CDS
<222> LOCATION: (1900)..(2026)
<221> NAME/KEY: CDS
<222> LOCATION: (2105)..(2230)
<221> NAME/KEY: CDS
<222> LOCATION: (2696)..(2833)

<400> SEQUENCE: 7
gatctgcgac ctccttcaga acctgccaaa atgactagga aaaatgctgt tccatagca      60 agagccaaaa gagaacatga cggccctgca ctccgggatc tctctggcac cagattccca   120
gcccagggga gacacctgaa ccccccagat ggtgacacac ctctgtggtc ctctgtcagg   180
gacataacct cccagcacag atttgcaaac tccctgctgc aggcacaagc agggctatcg   240
ggccccaggt gtggctcccc tgccttggtt cagggagtgg agacacagtt gcccactgct   300
ccccacccca ctgccaggcc tcttctgccc ccatgggtcc tggggtgggg gagccttggg   360
agttgaagaa tgcctctgac ccagattctt caagcagcct ctgagctcag aggaagagtc   420
tgcctcacgg cagcctccct gggtctagc tgtcaatcgc ccaggaagaa atacccagcg    480
cgggacccgg cggggaagct ggccttctct gtcttcccag gtgcagcaca gcgagtgtaa   540
ggagctgtct tgggcctgcc cagcctggtg ccctgcgggg gactgctggc acaggactgt   600
gactgggctt cagctctgtc tgaaaatctt tgcttcagag cacctcccta gtttgatctg   660
ataccccgcc tgaccctgcc agagtccaga ggtcacggcg ccagcccct gcctccggga    720 aggttattcc aaatgctccc acagccctga cccttcctgt tgctttgtcc cttgcagccc   780
aactcctctt tccgaccgcc gcagaaagac aaccccccaa gcctggtggc caaggcccag   840
tccttgccct cggaccagcc ggtgggg acc ttc agc cct ctg acc act tcg gat   894
                              Thr Phe Ser Pro Leu Thr Thr Ser Asp
                                1                   5 acc agc agc ccc cag aag tcc ctc cgc aca gcc ccg gcc aca ggc cag    942
Thr Ser Ser Pro Gln Lys Ser Leu Arg Thr Ala Pro Ala Thr Gly Gln
 10                  15                  20                  25
```

-continued

```
ctt cca ggc cgg tct tcc cca gcg gga tcc ccc cgc acc tgg cac gcc      990
Leu Pro Gly Arg Ser Ser Pro Ala Gly Ser Pro Arg Thr Trp His Ala
             30                  35                  40 cag atc agc acc agc aac ctg tac ctg ccc cag gac ccc acg gtt gcc     1038
Gln Ile Ser Thr Ser Asn Leu Tyr Leu Pro Gln Asp Pro Thr Val Ala
             45                  50                  55 aag ggt gcc ctg gct ggt gag gac aca ggt gtt gtg aca cat gag cag     1086
Lys Gly Ala Leu Ala Gly Glu Asp Thr Gly Val Val Thr His Glu Gln
             60                  65                  70 ttc aag gct gcg ctc agg atg gtg gtg gac cag ggt gac ccc cgg ctg     1134
Phe Lys Ala Ala Leu Arg Met Val Val Asp Gln Gly Asp Pro Arg Leu
    75                  80                  85 ctg ctg gac agc tac gtg aag att ggc gag ggc tcc acc ggc atc gtc     1182
Leu Leu Asp Ser Tyr Val Lys Ile Gly Glu Gly Ser Thr Gly Ile Val
90                  95                 100                 105 tgc ttg gcc cgg gaa gaa cac tcg ggc cgc cag gtg gcc gtc aag atg     1230
Cys Leu Ala Arg Glu Glu His Ser Gly Arg Gln Val Ala Val Lys Met
                110                 115                 120 atg gac ctc aga aag cag cag cgc agg gag ctg ctc ttc aac gag         1275
Met Asp Leu Arg Lys Gln Gln Arg Arg Glu Leu Leu Phe Asn Glu
            125                 130                 135 gtgggaggac aggtgggac acacacgggg gcgttgggga tgggcagtga gcagccagcc    1335
aggctggaca tctgtgagca ggggcagtgg gtggccatgc gtctgggcac tgtgcctggc   1395
actcaggccc ccacctgccc ccag gtg gtg atc atg cgg gac tac cag cac      1446
                        Val Val Ile Met Arg Asp Tyr Gln His
                                    140                 145 ttc aac gtg gtg gag atg tac aag agc tac ctg gtg ggc gag gag ctg     1494
Phe Asn Val Val Glu Met Tyr Lys Ser Tyr Leu Val Gly Glu Glu Leu
                150                 155                 160 tgg gtg ctc atg gag ttc ctg cag gga gga gcc ctc aca gac atc gtc     1542
Trp Val Leu Met Glu Phe Leu Gln Gly Gly Ala Leu Thr Asp Ile Val
            165                 170                 175 tcc caa gtc ag  gtgggcagct gggagggctg accctgagt gcaggctgcc          1593
Ser Gln Val Arg
        180 ctcaccatgg ccctgccagg gcaatgtggt cttctgcctg tggcccagaa gacttgggat   1653 gcctgggctc ccctgcctgc tgggtaact gagacccagg ggtcttggga gtggagaaga    1713 gaaggatagc ttctagccaa agctcaggcc ccagttttca ccagggctat ggcctgactg   1773 tgctgccaaa cagattgcct gggagctgtg gggcctagca ccaggactc ctactctgct    1833 cagccacccc acgacctgcc agagctaacg ttctctttca tcgggtggcc ccaccttcct   1893 gtccag g ctg aat gag gag cag att gcc act gtg tgt gag gct gtg ctg    1942
        Leu Asn Glu Glu Gln Ile Ala Thr Val Cys Glu Ala Val Leu
                    185                 190                 195 cag gcc ctg gcc tac ctg cat gct cag ggt gtc atc cac cgg gac atc     1990
Gln Ala Leu Ala Tyr Leu His Ala Gln Gly Val Ile His Arg Asp Ile
                200                 205                 210 aag agt gac tcc atc ctg ctg acc ctc gat ggc agg gtaggtccca          2036
Lys Ser Asp Ser Ile Leu Leu Thr Leu Asp Gly Arg
            215                 220 tcctgtccct ggcacagcca cgctcccact tcctcctgat ccaccactca ctcccttttc   2096 aaccgcag gtg aag ctc tcg gac ttc gga ttc tgt gct cag atc agc aaa    2146
         Val Lys Leu Ser Asp Phe Gly Phe Cys Ala Gln Ile Ser Lys
                 225                 230                 235 gac gtc cct aag agg aag tcc ctg gtg gga acc ccc tac tgg atg gct     2194
Asp Val Pro Lys Arg Lys Ser Leu Val Gly Thr Pro Tyr Trp Met Ala
```

-continued

```
                240                 245                 250
cct gaa gtg atc tcc agg tct ttg tat gcc act gag gtaaccgttc        2240
Pro Glu Val Ile Ser Arg Ser Leu Tyr Ala Thr Glu
    255                 260                 265 cctccacccc ccagacctcc caaaagcaac ttggcaactg cagctcttc tgctgtggcc  2300 cctccagtga gctcaccaaa agcagccctg gttttcagag tcccacctag tcaacaccct 2360
tccccctttc gatgggctg ctcttaccca gtgactttgc tgccaggaac gagtcctgca  2420
agtgctttcc tcagctcaag ggcagaatgg ggtatggccg ggcctcctat gtatgatggc 2480 cttttctctga gtgactgaca gctgtgtccc tataggcagt ggtcactcat gcaggcagta 2540
actggccaca gggcaggtga ccaggggagg aaggagacag acccaccaag gagagctggg 2600
gccagctgtc cccctccac cactgctgcc accagaacgc agctaccaat gggccagggt 2660
ctggccatgg ggtcagggac attttcctcc tgcag gtg gat atc tgg tct ctg    2713
                                        Val Asp Ile Trp Ser Leu
                                                            270 ggg atc atg gtg att gag atg gta gat ggg gag cca ccg tac ttc agt  2761
Gly Ile Met Val Ile Glu Met Val Asp Gly Glu Pro Pro Tyr Phe Ser
        275                 280                 285 gac tcc cca gtg caa gcc atg aag agg ctc cgg gac agc ccc cca ccc  2809
Asp Ser Pro Val Gln Ala Met Lys Arg Leu Arg Asp Ser Pro Pro Pro
    290                 295                 300 aag ctg aaa aac tct cac aag gtc agttggcaca aagggtgcg acctcgcaga   2863
Lys Leu Lys Asn Ser His Lys Val
    305                 310 ccccattcct cctgaggcaa ggggaccaga acctgggctc ccagcatctc ccttccactg 2923 aagccacagg gtctgggctc ctggaaaagg ctcctctttc cccacacaaa acccgcacct 2983 gggtgtggag ccgcatctac gcacaagttc gcatgtgcgc tccgacaagt cgcctcccac 3043 ggctgtggca ggagagttgc tgcttggcag aagggttgct gcttggcagg cactggtcgg 3103 aagcccagtg gggcccatga gcagggaaag ccaggacacc agcaactccc tgctgtccag 3163 ggagggatcc ggagaagctt cactgagcac aaacccttca acccgtgtcg ggagatccat 3223 accatgattc gatgtccctg tccatcacgg cgagtcggct catgctccat tcgttgcaca 3283 ccccgacaca gctaagccac agcgttcccc ttaaagccag tataagtgca tggaagtggt 3343 atacatgtaa cccttttgc caaatcggcc ccaaccccgc aggccttact gtggacgccc  3403
cctgctggca ggtcagcacg gggctgataa gtgcaccgc catctggtgg ccaaaacaag  3463
aaatgtctca gagggctgaa gcctctcctc taaaatagca aaaaaacaag agttctgtgg 3523 ccccaacaca aagctggatg ggaggaccaa caggaaacat cttccaagac aactggtcct 3583 tggagcccgc accgctaacc ccaaaattag catataaagc atgc                  3627
```

<210> SEQ ID NO 8
<211> LENGTH: 311
<212> TYPE: PRT
<213> ORGANISM: Homo sapiens

<400> SEQUENCE: 8

```
Thr Phe Ser Pro Leu Thr Thr Ser Asp Thr Ser Pro Gln Lys Ser
1               5                  10                  15

Leu Arg Thr Ala Pro Ala Thr Gly Gln Leu Pro Gly Arg Ser Ser Pro
            20                  25                  30

Ala Gly Ser Pro Arg Thr Trp His Ala Gln Ile Ser Thr Ser Asn Leu
        35                  40                  45
```

-continued

```
Tyr Leu Pro Gln Asp Pro Thr Val Ala Lys Gly Ala Leu Ala Gly Glu
 50                  55                  60
Asp Thr Gly Val Val Thr His Glu Gln Phe Lys Ala Ala Leu Arg Met
 65                  70                  75                  80
Val Val Asp Gln Gly Asp Pro Arg Leu Leu Asp Ser Tyr Val Lys
                 85                  90                  95
Ile Gly Glu Gly Ser Thr Gly Ile Val Cys Leu Ala Arg Glu His
                100                 105                 110
Ser Gly Arg Gln Val Ala Val Lys Met Met Asp Leu Arg Lys Gln Gln
                115                 120                 125
Arg Arg Glu Leu Leu Phe Asn Glu Val Val Ile Met Arg Asp Tyr Gln
130                 135                 140
His Phe Asn Val Val Glu Met Tyr Lys Ser Tyr Leu Val Gly Glu Glu
145                 150                 155                 160
Leu Trp Val Leu Met Glu Phe Leu Gln Gly Gly Ala Leu Thr Asp Ile
                165                 170                 175
Val Ser Gln Val Arg Leu Asn Glu Glu Gln Ile Ala Thr Val Cys Glu
                180                 185                 190
Ala Val Leu Gln Ala Leu Ala Tyr Leu His Ala Gln Gly Val Ile His
                195                 200                 205
Arg Asp Ile Lys Ser Asp Ser Ile Leu Leu Thr Leu Asp Gly Arg Val
210                 215                 220
Lys Leu Ser Asp Phe Gly Phe Cys Ala Gln Ile Ser Lys Asp Val Pro
225                 230                 235                 240
Lys Arg Lys Ser Leu Val Gly Thr Pro Tyr Trp Met Ala Pro Glu Val
                245                 250                 255
Ile Ser Arg Ser Leu Tyr Ala Thr Glu Val Asp Ile Trp Ser Leu Gly
                260                 265                 270
Ile Met Val Ile Glu Met Val Asp Gly Glu Pro Pro Tyr Phe Ser Asp
                275                 280                 285
Ser Pro Val Gln Ala Met Lys Arg Leu Arg Asp Ser Pro Pro Pro Lys
290                 295                 300
Leu Lys Asn Ser His Lys Val
305                 310
```

```
<210> SEQ ID NO 9
<211> LENGTH: 2669
<212> TYPE: DNA
<213> ORGANISM: Homo sapiens
<220> FEATURE:
<221> NAME/KEY: CDS
<222> LOCATION: (199)...(2244)

<400> SEQUENCE: 9
gagtgccgct tcctgggcta gagacaagca ccagcctgca gtggagaacg caggaccccg     60
ctgcccagaa ggagcagcca cggcctgcgg aggactggcc cagcaaggtc ccaggtcttc    120
cctctcctca gcgcctaaga gagagggccca gtgcgggtga ggagtcgcga ggaagaggcg    180
gaaggcgccg gaaggacc atg ttc cgc aag aaa aag aag aaa cgc cct gag       231
                    Met Phe Arg Lys Lys Lys Lys Lys Arg Pro Glu
                      1               5                  10 atc tca gcg cca cag aac ttc cag cac cgt gtc cac acc tcc ttc gac       279
Ile Ser Ala Pro Gln Asn Phe Gln His Arg Val His Thr Ser Phe Asp
            15                  20                  25 ccc aaa gaa ggc aag ttt gtg ggc ctc ccc cca caa tgg cag aac atc       327
Pro Lys Glu Gly Lys Phe Val Gly Leu Pro Pro Gln Trp Gln Asn Ile
```

```
            30                  35                  40
ctg gac aca ctg cgg cgc ccc aag ccc gtg gtg gac cct tcg cga atc      375
Leu Asp Thr Leu Arg Arg Pro Lys Pro Val Val Asp Pro Ser Arg Ile
         45                  50                  55 aca cgg gtg cag ctc cag ccc atg aag aca gtg gtg cgg ggc agc gcg      423
Thr Arg Val Gln Leu Gln Pro Met Lys Thr Val Val Arg Gly Ser Ala
 60                  65                  70                  75 atg cct gtg gat ggc tac atc tcg ggg ctg ctc aac gac atc cag aag      471
Met Pro Val Asp Gly Tyr Ile Ser Gly Leu Leu Asn Asp Ile Gln Lys
                 80                  85                  90 ttg tca gtc atc agc tcc aac acc ctg cgt ggt cgc agc ccc acc agc      519
Leu Ser Val Ile Ser Ser Asn Thr Leu Arg Gly Arg Ser Pro Thr Ser
             95                 100                 105 cgg cgg cgg gca cag tcc ctg ggg ctg ctg ggg gat gag cac tgg gcc      567
Arg Arg Arg Ala Gln Ser Leu Gly Leu Leu Gly Asp Glu His Trp Ala
         110                 115                 120 acc gac cca gac atg tac ctc cag agc ccc cag tct gag cgc act gac      615
Thr Asp Pro Asp Met Tyr Leu Gln Ser Pro Gln Ser Glu Arg Thr Asp
125                 130                 135 ccc cac ggc ctc tac ctc agc tgc aac ggg ggc aca cca gca ggc cac      663
Pro His Gly Leu Tyr Leu Ser Cys Asn Gly Gly Thr Pro Ala Gly His
140                 145                 150                 155 aag cag atg ccg tgg ccc gag cca cag agc cca cgg gtc ctg ccc aat      711
Lys Gln Met Pro Trp Pro Glu Pro Gln Ser Pro Arg Val Leu Pro Asn
                 160                 165                 170 ggg ctg gct gca aag gca cag tcc ctg ggc ccc gcc gag ttt cag ggt      759
Gly Leu Ala Ala Lys Ala Gln Ser Leu Gly Pro Ala Glu Phe Gln Gly
             175                 180                 185 gcc tcg cag cgc tgt ctg cag ctg ggt gcc tgc ctg cag agc tcc cca      807
Ala Ser Gln Arg Cys Leu Gln Leu Gly Ala Cys Leu Gln Ser Ser Pro
         190                 195                 200 cca gga gcc tcg ccc ccc acg ggc acc aat agg cat gga atg aag gct      855
Pro Gly Ala Ser Pro Pro Thr Gly Thr Asn Arg His Gly Met Lys Ala
205                 210                 215 gcc aag cat ggc tct gag gag gcc cgg cca cag tcc tgc ctg gtg ggc      903
Ala Lys His Gly Ser Glu Glu Ala Arg Pro Gln Ser Cys Leu Val Gly
220                 225                 230                 235 tca gcc aca ggc agg cca ggt ggg gaa ggc agc cct agc cct aag acc      951
Ser Ala Thr Gly Arg Pro Gly Gly Glu Gly Ser Pro Ser Pro Lys Thr
                 240                 245                 250 cgg gag agc agc ctg aag cgc agg cta ttc cga agc atg ttc ctg tcc      999
Arg Glu Ser Ser Leu Lys Arg Arg Leu Phe Arg Ser Met Phe Leu Ser
             255                 260                 265 act gct gcc aca gcc cct cca agc agc agc aag cca ggc cct cca cca     1047
Thr Ala Ala Thr Ala Pro Pro Ser Ser Ser Lys Pro Gly Pro Pro Pro
         270                 275                 280 cag agc aag ccc aac tcc tct ttc cga ccg ccg cag aaa gac aac ccc     1095
Gln Ser Lys Pro Asn Ser Ser Phe Arg Pro Pro Gln Lys Asp Asn Pro
285                 290                 295 cca agc ctg gtg gcc aag gcc cag tcc ttg ccc tcg gac cag ccg gtg     1143
Pro Ser Leu Val Ala Lys Ala Gln Ser Leu Pro Ser Asp Gln Pro Val
300                 305                 310                 315 ggg acc ttc agc cct ctg acc act tcg gat acc agc agc ccc cag aag     1191
Gly Thr Phe Ser Pro Leu Thr Thr Ser Asp Thr Ser Ser Pro Gln Lys
                 320                 325                 330 tcc ctc cgc aca gcc ccg gcc aca ggc cag ctt cca ggc cgg tct tcc     1239
Ser Leu Arg Thr Ala Pro Ala Thr Gly Gln Leu Pro Gly Arg Ser Ser
             335                 340                 345 cca gcg gga tcc ccc cgc acc tgg cac gcc cag atc agc acc agc aac     1287
```

-continued

| | | | | | | | | | | | | |
|---|---|---|---|---|---|---|---|---|---|---|---|---|
|Pro|Ala|Gly|Ser|Pro|Arg|Thr|Trp|His|Ala|Gln|Ile|Ser|Thr|Ser|Asn|
| |350| | | | |355| | | |360| | | | | |

```
ctg tac ctg ccc cag gac ccc acg gtt gcc aag ggt gcc ctg gct ggt      1335
Leu Tyr Leu Pro Gln Asp Pro Thr Val Ala Lys Gly Ala Leu Ala Gly
365                 370                 375 gag gac aca ggt gtt gtg aca cat gag cag ttc aag gct gcg ctc agg      1383
Glu Asp Thr Gly Val Val Thr His Glu Gln Phe Lys Ala Ala Leu Arg
380                 385                 390                 395 atg gtg gtg gac cag ggt gac ccc cgg ctg ctg ctg gac agc tac gtg      1431
Met Val Val Asp Gln Gly Asp Pro Arg Leu Leu Leu Asp Ser Tyr Val
            400                 405                 410 aag att ggc gag ggc tcc acc ggc atc gtc tgc ttg gcc cgg gag aag      1479
Lys Ile Gly Glu Gly Ser Thr Gly Ile Val Cys Leu Ala Arg Glu Lys
        415                 420                 425 cac tcg ggc cgc cag gtg gcc gtc aag atg atg gac ctc agg aag cag      1527
His Ser Gly Arg Gln Val Ala Val Lys Met Met Asp Leu Arg Lys Gln
            430                 435                 440 cag cgc agg gag ctg ctc ttc aac gag gtg gtg atc atg cgg gac tac      1575
Gln Arg Arg Glu Leu Leu Phe Asn Glu Val Val Ile Met Arg Asp Tyr
445                 450                 455 cag cac ttc aac gtg gtg gag atg tac aag agc tac ctg gtg gga gag      1623
Gln His Phe Asn Val Val Glu Met Tyr Lys Ser Tyr Leu Val Gly Glu
460                 465                 470                 475 gag ctg tgg gtg ctc atg gag ttc ctg cag gga gga gcc ctc aca gac      1671
Glu Leu Trp Val Leu Met Glu Phe Leu Gln Gly Gly Ala Leu Thr Asp
            480                 485                 490 atc gtc tcc caa gtc agg ctg aat gag gag cag att gcc act gtg tgt      1719
Ile Val Ser Gln Val Arg Leu Asn Glu Glu Gln Ile Ala Thr Val Cys
        495                 500                 505 gag gct gtg ctg cag gcc ctg gcc tac ctg cat gct cag ggt gtc atc      1767
Glu Ala Val Leu Gln Ala Leu Ala Tyr Leu His Ala Gln Gly Val Ile
            510                 515                 520 cac cgg gac atc aag agt gac tcc atc ctg ctg acc ctc gat ggc agg      1815
His Arg Asp Ile Lys Ser Asp Ser Ile Leu Leu Thr Leu Asp Gly Arg
525                 530                 535 gtg aag ctc tcg gac ttc gga ttc tgt gct cag atc agc aaa gac gtc      1863
Val Lys Leu Ser Asp Phe Gly Phe Cys Ala Gln Ile Ser Lys Asp Val
540                 545                 550                 555 cct aag agg aag tcc ctg gtg gga acc ccc tac tgg atg gct cct gaa      1911
Pro Lys Arg Lys Ser Leu Val Gly Thr Pro Tyr Trp Met Ala Pro Glu
            560                 565                 570 gtg atc tcc agg tct ttg tat gcc act gag gtg gat atc tgg tct ctg      1959
Val Ile Ser Arg Ser Leu Tyr Ala Thr Glu Val Asp Ile Trp Ser Leu
        575                 580                 585 ggc atc atg gtg att gag atg gta gat ggg gag cca ccg tac ttc agt      2007
Gly Ile Met Val Ile Glu Met Val Asp Gly Glu Pro Pro Tyr Phe Ser
            590                 595                 600 gac tcc cca gtg caa gcc atg aag agg ctc cgg gac agc ccc cca ccc      2055
Asp Ser Pro Val Gln Ala Met Lys Arg Leu Arg Asp Ser Pro Pro Pro
605                 610                 615 aag ctg aaa aac tct cac aag gtc tcc cca gtg ctg cga gac ttc ctg      2103
Lys Leu Lys Asn Ser His Lys Val Ser Pro Val Leu Arg Asp Phe Leu
620                 625                 630                 635 gag cgg atg ctg gtg cgg gac ccc caa gag aga gcc aca gcc cag gag      2151
Glu Arg Met Leu Val Arg Asp Pro Gln Glu Arg Ala Thr Ala Gln Glu
            640                 645                 650 ctc cta gac cac ccc ttc ctg ctg cag aca ggg cta cct gag tgc ctg      2199
Leu Leu Asp His Pro Phe Leu Leu Gln Thr Gly Leu Pro Glu Cys Leu
        655                 660                 665
```

-continued

```
gtg ccc ctg atc cag ctc tac cga aag cag acc tcc acc tgc tga         2244
Val Pro Leu Ile Gln Leu Tyr Arg Lys Gln Thr Ser Thr Cys  *
        670                 675                 680 gcccaccccca gtatgcctg ccacctacgc ccacaggcag ggcacactgg gcagccagcc   2304
tgccggcagg acttgcctgc ctcctcctct cagtattctc tccaaagatt gaaatgtgaa   2364
gccccagccc caccctctgc ccttcagcct actgggccag gccggacctg ccccctcagt   2424
gtctctccct cccgagtccc caagatggag acccctttct acaggatgac cccttgatat   2484
ttgcacaggg atatttctaa gaaacgcaga ggccagcgtt cctggcctct gcagccaaca   2544
cagtagaaaa ggctgctgtg gttttttaaa ggcagttgtc cactagtgtc ctaggccact   2604
gcagagggca gactgctggt ctccacagat acctgctgtt ctcagctcca gcttcaaacc   2664
tcgag                                                              2669
```

<210> SEQ ID NO 10
<211> LENGTH: 681
<212> TYPE: PRT
<213> ORGANISM: Homo sapiens

<400> SEQUENCE: 10

```
Met Phe Arg Lys Lys Lys Lys Arg Pro Glu Ile Ser Ala Pro Gln
 1               5                  10                  15

Asn Phe Gln His Arg Val His Thr Ser Phe Asp Pro Lys Glu Gly Lys
             20                  25                  30

Phe Val Gly Leu Pro Pro Gln Trp Gln Asn Ile Leu Asp Thr Leu Arg
         35                  40                  45

Arg Pro Lys Pro Val Val Asp Pro Ser Arg Ile Thr Arg Val Gln Leu
     50                  55                  60

Gln Pro Met Lys Thr Val Val Arg Gly Ser Ala Met Pro Val Asp Gly
 65                  70                  75                  80

Tyr Ile Ser Gly Leu Leu Asn Asp Ile Gln Lys Leu Ser Val Ile Ser
                 85                  90                  95

Ser Asn Thr Leu Arg Gly Arg Ser Pro Thr Ser Arg Arg Ala Gln
             100                 105                 110

Ser Leu Gly Leu Leu Gly Asp Glu His Trp Ala Thr Asp Pro Asp Met
         115                 120                 125

Tyr Leu Gln Ser Pro Gln Ser Glu Arg Thr Asp Pro His Gly Leu Tyr
     130                 135                 140

Leu Ser Cys Asn Gly Gly Thr Pro Ala Gly His Lys Gln Met Pro Trp
145                 150                 155                 160

Pro Glu Pro Gln Ser Pro Arg Val Leu Pro Asn Gly Leu Ala Ala Lys
                165                 170                 175

Ala Gln Ser Leu Gly Pro Ala Glu Phe Gln Gly Ala Ser Gln Arg Cys
            180                 185                 190

Leu Gln Leu Gly Ala Cys Leu Gln Ser Pro Pro Gly Ala Ser Pro
        195                 200                 205

Pro Thr Gly Thr Asn Arg His Gly Met Lys Ala Ala Lys His Gly Ser
    210                 215                 220

Glu Glu Ala Arg Pro Gln Ser Cys Leu Val Gly Ser Ala Thr Gly Arg
225                 230                 235                 240

Pro Gly Gly Glu Gly Ser Pro Ser Pro Lys Thr Arg Glu Ser Ser Leu
                245                 250                 255

Lys Arg Arg Leu Phe Arg Ser Met Phe Leu Ser Thr Ala Ala Thr Ala
            260                 265                 270
```

```
Pro Pro Ser Ser Ser Lys Pro Gly Pro Pro Gln Ser Lys Pro Asn
        275                 280                 285

Ser Ser Phe Arg Pro Pro Gln Lys Asp Asn Pro Pro Ser Leu Val Ala
        290                 295                 300

Lys Ala Gln Ser Leu Pro Ser Asp Gln Pro Val Gly Thr Phe Ser Pro
305                 310                 315                 320

Leu Thr Thr Ser Asp Thr Ser Ser Pro Gln Lys Ser Leu Arg Thr Ala
                325                 330                 335

Pro Ala Thr Gly Gln Leu Pro Gly Arg Ser Ser Pro Ala Gly Ser Pro
                340                 345                 350

Arg Thr Trp His Ala Gln Ile Ser Thr Ser Asn Leu Tyr Leu Pro Gln
        355                 360                 365

Asp Pro Thr Val Ala Lys Gly Ala Leu Ala Gly Glu Asp Thr Gly Val
370                 375                 380

Val Thr His Glu Gln Phe Lys Ala Ala Leu Arg Met Val Val Asp Gln
385                 390                 395                 400

Gly Asp Pro Arg Leu Leu Asp Ser Tyr Val Lys Ile Gly Glu Gly
                405                 410                 415

Ser Thr Gly Ile Val Cys Leu Ala Arg Glu Lys His Ser Gly Arg Gln
                420                 425                 430

Val Ala Val Lys Met Met Asp Leu Arg Lys Gln Gln Arg Arg Glu Leu
        435                 440                 445

Leu Phe Asn Glu Val Val Ile Met Arg Asp Tyr Gln His Phe Asn Val
        450                 455                 460

Val Glu Met Tyr Lys Ser Tyr Leu Val Gly Glu Leu Trp Val Leu
465                 470                 475                 480

Met Glu Phe Leu Gln Gly Gly Ala Leu Thr Asp Ile Val Ser Gln Val
                485                 490                 495

Arg Leu Asn Glu Glu Gln Ile Ala Thr Val Cys Glu Ala Val Leu Gln
                500                 505                 510

Ala Leu Ala Tyr Leu His Ala Gln Gly Val Ile His Arg Asp Ile Lys
        515                 520                 525

Ser Asp Ser Ile Leu Leu Thr Leu Asp Gly Arg Val Lys Leu Ser Asp
530                 535                 540

Phe Gly Phe Cys Ala Gln Ile Ser Lys Asp Val Pro Lys Arg Lys Ser
545                 550                 555                 560

Leu Val Gly Thr Pro Tyr Trp Met Ala Pro Glu Val Ile Ser Arg Ser
                565                 570                 575

Leu Tyr Ala Thr Glu Val Asp Ile Trp Ser Leu Gly Ile Met Val Ile
                580                 585                 590

Glu Met Val Asp Gly Glu Pro Pro Tyr Phe Ser Asp Ser Pro Val Gln
        595                 600                 605

Ala Met Lys Arg Leu Arg Asp Ser Pro Pro Lys Leu Lys Asn Ser
610                 615                 620

His Lys Val Ser Pro Val Leu Arg Asp Phe Leu Glu Arg Met Leu Val
625                 630                 635                 640

Arg Asp Pro Gln Glu Arg Ala Thr Ala Gln Glu Leu Leu Asp His Pro
                645                 650                 655

Phe Leu Leu Gln Thr Gly Leu Pro Glu Cys Leu Val Pro Leu Ile Gln
                660                 665                 670

Leu Tyr Arg Lys Gln Thr Ser Thr Cys
        675                 680
```

-continued

```
<210> SEQ ID NO 11
<211> LENGTH: 19038
<212> TYPE: DNA
<213> ORGANISM: Homo sapiens
<220> FEATURE:
<221> NAME/KEY: misc_feature
<222> LOCATION: 453
<223> OTHER INFORMATION: n = A,T,C or G

<400> SEQUENCE: 11
tccccaccaa aaaattgtgc ccaagaaacc gtcgtgttcc cctgtgccaa ggtttcggtt      60
ttaaagaaac cccccaaaca gggaaacctt ctttcttaaa ttggtttggg tgtgaacctt     120
tcccttccaa gtcttgggca tcccccaaa tcaattcatg cgttagccaa ccagaaaaat      180
gcctgcaacc atccaaaaga aaaagttaa aagcagtctc accacaggca agtgcttttc      240
aagcttaggt tgaattctca agtgtgccct ccttcccctg tgttaagcca aagtttcagc     300 cagaagggc ttgggcctgt gcccaacctg cccaccccg ttttgctttg tttccacttc       360
agggtctaag gctcacatca tctcttttca agctggcaag gagaaacggc agggtctggc     420
tctctgaggg ggagtccctt tctttcttct tcntggtgtc tctttgtagg aaagctcctc     480
ccctagatga attgcgtgca gatggagatg ctagaggggc gacagtaaca gctggcatgg     540
cctgtttgac ttaaccttgg ggccccatgg ctggtcagc agccacctcc ctcagcccag      600
tggccttgga gacatggatg ggaaaaggag ccctggaaat ggcaagcgga ggccctggct     660
gaccgggtgg gagtgctctg aggacacagc ctgatgctgg ggagaggcag ggcatgtttt     720
gtcctgggtg attcactcgc gatgactggg gcaacactgg tcccgttcag gtggatgaac     780
gtctcttagg cactcagcct ccatggatca ctcttctctg tatttaaaaa tattttgttt     840
ttggccggac gcggtggctc acgcctgtaa tcccagcact tgggaggct gaaggcgggt      900 ggatcacctg aggtcaggag ttcaagatca gcccagccaa catggtgaaa ccctatctct     960
actaaaaata caaaaattag ccggacgtgg tggtgcacac ctatagtctc agctacttgg    1020
gaggctgagg caggagaatc acttgaacct ggaaggcaga ggttgcagtg agccaagatc    1080
gcaccactgt actccagcct gggcaacaga gtgaaacgct gtctcaaaaa aaaaaaaaaa    1140 aaaaaaaat tgttttttt tagagaagca atccgtcgtc tttaaggaaa acttagaaaa       1200
agagtagaaa gatagaatag aaggagatca cctgtagccc caccaggtaa atgggacaac    1260
taatatgttg atgtatttcc ttcaaatagc cattgtattc acactgcatt gacaaattac    1320
cattggcaaa atctttaaaa accccctacc cctaatctat atcatcaaga attccacttt    1380
cgccaaagta aaccttgata gtttaatttg tgtctgggac ccatgactgt ggacaggttt    1440
aggccccagc aggtcgtggg atccaggaga gaccaccaaa tcgggcccct cataatgatc    1500
acactagacc tgagggaggt gagagtcagg ctacgggtac ccgccgtcac tcccaccagc    1560
tttattattt tacctttcac attgagggtt gtgatctgtc tgcataattt tggagtatga    1620
tatgagctca ttcttccggg tttatttttt ttccatgcag atatcaaatt acttcagcta    1680
catttattaa aaacatcatc cattccccca gcatgttgca gggtcacctt tgtcattaat    1740
caaatgacct cataagagtg ggtctatttt tggattctct cttctgttcc attggtctat    1800
ttgtcaattc cgtactaaat ttgccaattt ttgcctattt gcctattgcc tatttgccaa    1860
ttccatacta aattaattat tgtagctttc taataaatct taatatctat ttagtacaat    1920
cctccaactt cgttcattaa gattgtcttg gctattcctg gttctttata tttctgtata    1980
cattttagaa tcagttcatc aatttctacc aaaggaaata tgctgggatt ttgtttgaga    2040
```

```
tttaaattaa tctgcaggtt aacttgggaa taattgacat cttttacagta ttgaaccttc   2100 tcatctatga acattcttta atatctttaa taatgttttg tattttccaa tataaggact   2160
ttgtattttt ttgttagatt tattctagat attttgtatt tttaatgtaa aatgatatct   2220
ttttaaaaat ttcattttt tttttgagac agagtctcgc tctgtcgccc aggctggaat    2280
gcagtggcct gatctcagct cactgcaagc tccgcctccc aggttcacgc cattctcctg   2340
cctcagcctc ctgagtagct gggactacag gtgcccacca ccacacccgg ctaatgtttt   2400
gtagttttag tagagacggg gtttcaccgt gttagccagg atgatctcta tctcctgacc   2460
tcgtgattcg cccacctcgg cctcccaaag tgctgggatt acaggcgtga gccaccgcgc   2520
ctggcccttt ttaaaaattt catgttgtta ctggtatgta gaaatccagt tgattttta    2580 aaatattgac cttgagcctg gcacggtgg ctcatgcctg taatcccagc actttgggag    2640
gctgaggcgg gtggatcatg aagtcaagag atcgagacca tcctggccaa catggtgaaa   2700
ccccatctct actaaaaata caaaaattag ctgggcgtga tggcgtgcgc ctgtagtccc   2760
agctactcag taggctaagg caggagaatc acttgaaccc gggaggcaga gattgcagtg   2820
agctgagatc acaccactgc actccagccc gggcaagaca gcgagactcc atctcaaaaa   2880
atatatatat atatattgac cttgaatcag ggaccttcta aattcactcc cttaatccca   2940
gttttatgta gattctcccg cattttctac ttacacagtt atgttgtccc acacagtgtt   3000
ggcctcacca catttcagat gagtcctagc tgcctcctt taggtggttg attggttgat    3060
tttccagacc taagtgatgg cctctggttt ctaaagctct actccctagc ccccaaagcc   3120
tgagctcagc tgattgcttc tgccaactcc caccctcacc atcaccactc ctggccctgg   3180
gacaccctct gggctgtcct tctttcttct ccagcctccc tgctgcctct gggaagaact   3240
tgttccggaa tggctcacta ttagaatgga ctcaagagag gctcccagag tcagagacca   3300
tttgctaaag atgctctccc tgtgcatccc cacagcaaaa gctgagcgct tgggtggggc   3360
aggggagttg gggagagggc tgttctgggg tgggtggtgg ggggccggtt caccagctct   3420
tcttcagctg cagtctgtgt ccctgcacct ccagaagatt tcacagagct agggaggagg   3480
gcgaaacagg cagctcaact aatccaggga tagcaggtct atccaaggga ctgggggaat   3540
agacctgctg aataaagact cttctgtagc aaaaggcaaa ggctgtaatc ccagcacttt   3600
gggagaccaa ggcaggtgga tcatttgaag tcagaagttc gagaccagcc tggccaacat   3660
ggtgaaatcc cgtctctact aaaaatacaa aaattagccg ggtatgttgg tgggtgcctg   3720
taatctcagc tattcaggag gctgaggcaa gagaatcact tgaacccggg aggtggaggt   3780
tgcagtgagc ccagatggtg ccactacact ccagtctggg cgacagggcg gcaagactcc   3840
ttctcaaaaa caacaacaac aacaacaaac aacaacaaaa aaggcaaagg ccaaaaggag   3900
gaggacaaat tttaccaaac catgatgtat atatggcgag gtccccaggt cccagacccc   3960
tgacatcagg catgaccct ttgactggta agtctgagca gaaagtggtt tggtgttact    4020
cccagacttg tatctgccca agtgccagtg tctggagggc ctgagcttca agacagggat   4080
tcaaagagag gtgacatcac aagagaaaca accgtcatgt atgggactc tgcttacttc    4140 acacacccta aaccctatga gctgtctttc attaaccccc ctggctcaga tcatttcagt   4200
tatttgttca aaatctctcc aaattattag tgggagactc cctacaactc atctgcaact   4260
cacacaggtt gttttattcc aaagggcttg gtctgtaagg gtcctgtaca tgtggctcta   4320
cctctagggg gtgttcggtg gatcccgaac ctcaagaccc agaagcatgg ctgacattga   4380
gatgtgacgt gggctctgat tgagtcacgc atggtgaatt cctagtgggg aaccactggc   4440
```

-continued

```
tgtccagggt ccctgccttt ctgccagctg cctcccagat ctgcgacctc cttcagaacc    4500
tgccaaaatg actaggaaaa tgctgtttcc atagcaagag ccaaaagaga acatgacggc    4560
cctgcactcc agatcttcgg gcggatgagt aatccaagct ttcagttcaa gaatcatgtt    4620
tcagtttctt gaagcctgga agtgaccttt tcagatacat aagaacccag tgagctgttc    4680
tgagcctctt cagatccaaa agcattcaag aggcagccct ggccctgtct gccatcaaca    4740
tgtgatccca ggtccgggat ccctgaagg cgaaactaga gcaacccttt ggaagtgtcc    4800
ctccccttcc caggccccca gttccccact ctcagatcta cccatgctat ccattgcaag    4860
cctgtgtcac ttctgtgtat gcagctcagc acgaccttag gcaaagccag aatcagcaag    4920
gcacgggaca caggcttgat tgcaggttaa gtgttttatt gtttgttttt tgagacagag    4980
tctcattctg ttgcccaggc tggagtgcag tggggcaatc tcagctcact gcagcctcag    5040
cctcctgggt tcaagcgatt ctcctccctc aacccatgg gtatccggga ctacaggcac    5100
gtgccaccag gcccggctaa tttctttgta tttttagtca agacaggttt tcaccatgtt    5160
ggccaagctg gtctcaaact cctgacctca ggtgatccac cgcctcggc ctcccagagt    5220 actaggatta caggcatgaa ccaccatgcc cggcccaggt gatgttttac atagagctcc    5280
aataccagag agaagagtgt caaggggagg tggtgctctc tgccttctct ggagagcttt    5340
acccctaagt tagctgcccc tcacccaccc caggctatcc tcttggctca gggcctttct    5400
ggaattgagg taaagcacat ggtaaccatg aaggcccttt gggggctccc tgatacataa    5460
tagtcccaca ccgggcagca tgtctgtgat cagctggttg gcttttt att aacgtatcat    5520 attaacaggt tcaaccatcc tgggacaaag ctgagttgta ataaaaaaaa aaagccaaca    5580
aaaaaataac tttaatatac tgttggattc aattcgatag ttttaagatt ttcatagtta    5640
cgttcctaaa tgatattgag tcaaattttc cttttcttgc actctcctta tctggtttta    5700
agaatcaagg tcatactcgt ttcataaaac aagcttgcta actttcctcc ctctttcccc    5760
atttttaaaa ttcgttgaca gacagtggaa tgatacttgt aatgggcttt ggattttata    5820
aaaacacacc cccagagtct gcctgctcca taggggactt ggcacaggca agaagacacc    5880
tcttttcctt gtttatagtc tgcactggct tatttatggc acgtttgttg tttctgggac    5940
tgttctgctg ggagccagcc atttccctga ggaagcagag atgaaggtgc aggcaagccc    6000
taggcttcta ggggagctgt gctgggggag gggagggagc cctgaacctg gtgccccagg    6060
ccctgctgca gccaccccctc tttccgggga gggagctcaa ccttactctg cacttacagg    6120
caccatgttc cgcaagaaaa agaagaaacg ccctgagatc tcagcgccac agaacttcca    6180
gcaccgtgtc cacacctcct tcgacccaa agaaggcaag tttgtgggcc tcccccaca    6240 atggcagaac atcctggaca cactgcggcg ccccaagccc gtggtggacc cttcgcgaat    6300
cacacgggtg cagctccagc ccatgaaggt aagaggggcc ggcagggatg aggttcagcc    6360
tctcccagta ctcagacaac catgcctggc taaacctcag aaaggcccct ggaggaacca    6420
cctacttcac agctatcagt taatcagctg ttttaactcc ctgcctgtca gcctgccatt    6480
ctctccctgg gtaagccagg gcgaaggagg ctggggagac cctctctgca gggtggtggg    6540
gttgccagat tcagcacatg aaaatgtgag atgctcaatt gcatttgtat ttcagatgac    6600
aacgaatagt ctttttaggac gtgtcccatt caatatttgg acctgcagcc ccatagggac    6660
tgagggctct cccagaccag gagaattttta gttgtgaggg tcacgactag tagacccaag    6720
agcctggtag aaggtggggt caggggccct atcagggttt ggaggctgcg aagccagtgt    6780
```

```
gtgtggagga gccccggcc tggtgtctct tcctcagagg gctgggcaca tctctcccag    6840
ccacccgtgg agctagagaa tggagccccg ccccctgagc tccagctccc tggcccagcc    6900
gaccacaccc ctgggcatgc tggatgcagc cccatggcac tcaccatctg ctctgctgac    6960
gctgggcctt ctccccgcat ccctgcatcc agcacaggcg ggacccacgg tgggccctga    7020
taaattatgg aaaaattaat gggtggatga cacagcaggg aaggtcctta ggtggtcctc    7080
cccagggccc ccaggacat tctctgaccc tgatctccca gccaccctc cctgccacaa       7140 ttgggcagct cccacacact cttttctctt cccctacag acagtggtgc ggggcagcgc     7200
gatgcctgtg gatggctaca tctcggggct gctcaacgac atccagaagt tgtcagtcat    7260
cagctccaac accctgcgtg ccgcagccc caccagccgg cggcgggcac agtccctggg      7320
gctgctgggg gatgagcact gggccaccga cccagacatg tacctccaga gcccccagtc    7380
tgagcgcact gaccccacg gcctctacct cagctgcaac gggggcacac cagcaggcca     7440
caagcagatg ccgtggcccg agccacagag cccacgggtc ctgcccaatg ggctggctgc    7500
aaaggcacag tccctgggcc ccgccgagtt tcagggtgcc tcgcagcgct gtctgcagct    7560
gggtgcctgc ctgcagagct ccccaccagg agcctcgccc ccacgggca ccaataggca      7620 tggaatgaag gctgccaagc atggctctga ggaggcccgg ccacagtcct gcctggtggg    7680
ctcagccaca ggcaggccag gtggggaagg cagccctagc cctaagaccc gggagagcag    7740
cctgaagcgc aggctattcc gaagcatgtt cctgtccact gctgccacag cccctccaag    7800
cagcagcaag ccaggccctc caccacagag caaggtaagt caggagcctg gcctgcaggt    7860
gtccactggg gagtgggtgt agggacacag gccttgccta gccttcccct tggaggactg    7920
gcaaagaggc tccctggact gcttccgcct aaggcggcag aaatgtgcac ggtaacctct    7980
tctctaagga gggtggctcg cctcctcctt ccctccttc ctttccttct tttctctgtg      8040
gctgttgtgt tgtttcccat ttctgtcagt atttgttccc aagtgtgtgg ccataggaaa    8100
agctggattt gcctagtcca ggggcagcag gaggccgact tgtggcatgt gtgactgctt    8160
cagacgcaca ttttcttgt gagaaaggaa agggtgaagg gagccccgt ggtgacattt        8220 cttggcaggc agagtggagc gcacctttt gcttcttcca ggccctccag catcctgttg      8280
atagtgacag taacctcttt tcccatttgg cagaggagga gactgataga gagagggtga    8340
gtcaccccca ggcatgatgg agagtgagtc agagaaggaa ggtggggagt gctctggggc    8400
tgcctgtccg gcccgggccc tcttggctca tgactcttgc gtatgaaggc tttacaagca    8460
cagcagccac ttgttctttta gctccttcct gggagggtca aaggcagtcc taagaaacgg    8520
ctgctgacag tggcatgggt aatggagcct ccctccctc ctgggagggc tttaagacaa      8580
gcctgggtac tcccctgtca tcggtggggt gagtgtggcc cagcctgcac agggtgtggg    8640
tttggggatg acccggacta caacctctct gggtcactgc ctgccagctg aggtactcag    8700
agaaagttct gggcggccgc gcgtggtggc tcacgtctgt agtcccagca ctttgggagg    8760
ccaaggtgga tggtcacga ggtcaggaga tcgagaccat cctcgctaac acggtgaaac       8820
cccgtctcta ctaaaaatac aaaaaaaatt agccgggcgc ggtggcgggc gcctgtagtc    8880
caagctactc aggaggctga ggcaggagaa tggcgtgaac ccgggaggca gagcttgccg    8940
tgagctgaga tcgcaccact gcactccagc ctggggaca gacagagcga gactccgtct      9000
caaaaaaaaa agagaaagtt ctgagctttg tgcactctag tcccctacta ggttaaagga    9060
cagtgggttg ggatcccat gggttgtggc ttgatgtatc tgtgagagga acacgagcat       9120
ctgtgagctg cagggtgtct ggaaggctgt gccctgggg agactcagcc agaaaaccaa       9180
```

```
cgtaagatca ggacagtgca ccctgctggg aaggtgagat tcggagcttg acctccctct      9240
gtctctcagg agtcctgctg cgaggcctca gggatttgga gaaagggtt gtcaacactg       9300 ggctgggcac tcatttgcat cttttctggc tcctgccagc accccacagc agggggagag      9360
gcctgtccat ccctgcacaa tgtactgagt actcaccatg gccactgct gctgggtatg       9420 ccgggatgtc ccccatactt gtgggagcag gcggtagtta tctcgagctc agcaacacca      9480
tacttccaaa tccaggggag tggtttcctt ctgggcaact cagacacatc tttcaagatt      9540
tctactctga agccaagcct ctcaatggca agctgagacc ccccgagctg ctccgggccg      9600
gggcttctca gcgtcctcac tgcaggcgct caggtcagtc catccttttgt ggtgggctct     9660 ccttgcactg tagcagcctc cctggcctct actcactaga agttggtggt accctcggtt      9720
ggaataacca aaaatgcctc cagacactgc caaatgtcac tcgagcacac ccattaagaa      9780
ccactgcctt aagcaaattc aataacagat ggggagcatc agccttcctc ctcctcctcc      9840
accaccacct accccaggag tccccagatc aagccagcag cccttggcac tggggctgac      9900
tctggacact tgcagcagct tccataacag cagttaggcc acagaggcca tgcagtgtgc      9960
caggcatggc tgcaggaggg tctgagtata gactccaggg ctcctgtacc tagccccagg     10020
cagtgaggcc tggagtcact ctagctaaag agatcaggaa gacagggcgt gggggcacag     10080
agaccaaaga ggcaagacag ttttttagga gcttgcaggg attagacatg ttccacttag     10140
agtcagaagg gcaaacattg gttaagcacc taccgtgtac tccgatatat gtcaaggata     10200
catggcacca gtgggattgc agcatgggag tcagcagcca cgggcgtcct gcgggttcca     10260
gtgcctacag gacaaccaaa caacccacag ggttatgagg attacatgag atagtacgtt     10320
gaaggcactt gtcaaagtgg taagccctca ataaatggct ttattagtag tatttgagat     10380
ggcgtctccc tctttcgccc aggctggagt gcagtggcac aatcttggct cactgcaacc     10440
tccacctcct gggttcaagt gatcctccca ccttagcctc ccaagtagct gggattacag     10500
gcacgctcca ccatacccaa ctaatttttg tattttttaga agagatgggg tttcaccatg     10560
ttgcccaggc tggtcttgaa ctcctgacct caagtgatcc acctgccttg gcctcccaaa     10620
gtgctgggat tacaggcacc tgagccacca tgccaggccg gctttattat ttttaaaaat     10680
attatgccat ggcctctccc ctttaggata cttaaggtat agcccctaa gcccacagct     10740 ggggagccat ggctcagggc gggaaatgag gcattgctgt aaatgtatgc atgactcttc     10800
tagtggcttt cttcccaaga ggtctatcac atgagtaact tcagaattaa tccagagcct     10860
gtaacaatta attaattctg ttgtcgtgtc ccccttttccc tttcttgtgt ggcctcacaa     10920
gtttcatctg gtccttgctt tgtgattacat tgataaaagc tccctccctg tggagacagg    10980
cagtgaagcc aacgaaagga tgctagagac cagaccttgc caggctgaag accaagccag    11040
ctccccagac tccccagcct atgtcccaga ctctgcttgt gctgggctcc tggctgggcc    11100
atccctcccc cagcctccag acgcaggctc cgccctgagc ccagccagca cctgcagcag    11160
cagcagcagc acagggacct ggcctgtgga gacaggaag aaaccccctac ctcagcctgt    11220 ccacgtggta cccacacatc ctcagagtag agctggccca tgcagaagcc ctcaaggcca    11280
ggaggggaat gatctcattt tacagccttt cttaggagct tcaggatgag aggtcatcag    11340
agccacctca ggaggagctt taggtggtcc ccaagcttct gccccgaccc acctggatgg    11400
gtgcctggag agcatgtttt ctgagttaag tccacactca ggccagcagg cagcttcctt    11460
agagccccga gcctttctac aggttgactg tgtgatgcag tgagccctgc cccacttccc    11520
```

```
tccctgtccc tgcctggtga cgtctcatgg aacctctgtt cccaggacct ggtatcacag    11580
cctcagtcat ggccatgcgc cctccacccc cctcacagcc ctcccagagg ctccctgagg    11640
ccgtaagatc atactgccca cttatgcaga gtttctcaaa gtatgttcca tgggcctcct    11700
aggacccagg gaccttgttc aaatgcagtc tctgctctag gctcccaccg aatcaggctc    11760
tgaggcggga agtctgcggt ttctctagct ccccagatct ctgcacacgt ccctgcattg    11820
tagtggagac aggctcagag aggatgactt gcctaaggct catcacaggg cagagcagcc    11880
cagggctggg ccccaggtcc tgacagccca gtccaggggt cccactgctc cactacacag    11940
tggatggtga cagtgtcaca gtgtcacagt ggatggtgac agtcaggtgc tggcgaggac    12000
atgggagaat gtttactgtc caaatgtact catcagggat ggagtgagtc caggcagtcc    12060
tgggaggatt gctagcttct ttcctgtgaa ggtcaagcac acactcgggt gggcaggcag    12120
gtgtgggggt ggcagaagtc tgccccagca tggctgtcgg ccagcaggag tgcctattcc    12180
accctaagca ggccagggac ttggctggag agtagaagcc ctgaagctgc gggggtcgg    12240 ggaaggaagg gagtgagggt tgccaaagac actgaaaaga ctctggtggg gcccaaggcc    12300
cagatttggg gtttggggtc cctgagcaag catcccagcc caaacttact gcttgagatt    12360
tcctgtaagt tgtttcagct atgggatcag gaccaggacc cactgggcac ctaagacaat    12420
ggcttacatg atgggtttgg agaagttcct agaaggcttt ttctgcatcc cctgaagcat    12480
ccctctccag gtgccctta aaaacacgta atccctggga ggggtcatgg tgcatatcac    12540
cgctccttgg ggagaaccca agatgggcg ggcacctttc ctgtcagaaa gagcagaagg    12600
gcttgggctc ggaaaagcaa gaagcctcgc aggcttccag ggctgggcct gagcagggct    12660
cactgggggc ccaggctgcc cctcagctcc accttccctt cctccctccc tgccagagcc    12720
aatgaggata ggcccctac cttctcctcc ctcccggggg ctccttagcc aggagtttca    12780
tgccagggag gaagtggaag gactccttta gggggtcctt aagacatctc cccatccctg    12840
gcctcaaggc ttgggtttgg ctggacctac cctcctaact ccagatctct ctggcaccag    12900
attcccagcc caggggagac acctgagaac cccccagatg gtgacacacc tctgtggtcc    12960
tctgtcaggg acataacctc ccagcacaga tttgcaaact ccctgctgca ggcacaggca    13020
gggctatcgg gccccaggtg tggctcccct gccttggttc agggagtgga cacacagttg    13080
cccactgctc cccacccac tgccaggcct cttctgcccc catgggtcct ggggtggggg    13140
agccttggga gtgaagaatg cctctgaccc agattcttca agcagcctct gagctcagag    13200
gaagagtctg cctcacggca gcctccctgg ggtctagctg tcaatcgccc aggaagaaat    13260
acccagcgca ggaccggcg gggagctggc cttctctgtc ttcccaggtg cagcagagcg    13320
agtgtaagga gctgtcttgg gcctgccag cctggtgccc tgcgggggac tgctggcaca    13380
ggactgtgac tgggcttcag ctctgtctga aaatctttgc tcagagcacc tccctagttt    13440
gatctgatac cccgcctgac cctgccagag tccagaggtc acggcggcca gcccctgcct    13500
ccgggaaggt tattccaaat gctcccacag ccctgaccct tcctgttgct tgtccctgc    13560 agcccaactc ctctttccga ccgccgcaga aagacaaccc cccaagcctg gtggccaagg    13620
cccagtcctt gcctcggac cagccggtgg ggaccttcag ccctctgacc acttcggata    13680
ccagcagccc ccagaagtcc ctccgcacag ccccggccac aggccagctt ccaggccggt    13740
cttccccagc gggatccccc cgcacctggc acgcccagat cagcaccagc aacctgtacc    13800
tgccccagga ccccacggtt gccaagggtg ccctggctgg tgaggacaca ggtgttgtga    13860
cacatgagca gttcaaggct gcgctcagga tggtggtgga ccagggtgac cccggctgc    13920
```

-continued

```
tgctggacag ctacgtgaag attggcgagg gctccaccgg catcgtctgc ttggcccggg    13980
agaagcactc gggccgccag gtggccgtca agatgatgga cctcaggaag cagcagcgca    14040
gggagctgct cttcaacgag gtgggaggac agggtgggac acagacgggg gcgttgggga    14100
tgggcagtga gcagccagcc aggctggaca tctgtgagca ggggcagtgg gtggccatgc    14160
gtctgggcac tgtgcctggc actcaggccc ccgcctgccc ccaggtggtg atcatgcggg    14220
actaccagca cttcaacgtg gtggagatgt acaagagcta cctggtgggc gaggagctgt    14280
gggtgctcat ggagttcctg cagggaggag ccctcacaga catcgtctcc caagtcaggt    14340
gggcagctgg gagggctgga ccctgagtgc aggctgccct caccatggcc ctgccagggc    14400
aatgtggtct tctgcctgtg gcccagaaga cttgggatgc ctgggctccc ctgcctgctg    14460
gggtaactga gacccagggg tcttgggagt ggagaagaga aggatagctt ctagccaaag    14520
ctcaggcccc agttttcacc agggctatgg cctgactgtg ctgccaaaca gattgcctgg    14580
gagctgtggg gcctagcacc agggactcct actctgctca gccaccccac gacctgccag    14640
agctaacgtt ctcttctcatc gggtggcccc accttcctgt ccaggctgaa tgaggagcag    14700
attgccactg tgtgtgaggc tgtgctgcag gccctggcct acctgcatgc tcagggtgtc    14760
atccaccggg acatcaagag tgactccatc ctgctgaccc tcgatggcag ggtaggtccc    14820
atcctgtccc tggcacagcc acgctcccac ttcctcctga tccaccactc actcccttt    14880 caaccgcagg tgaagctctc ggacttcgga ttctgtgctc agatcagcaa agacgtccct    14940
aagaggaagt ccctggtggg aacccctac tggatggctc ctgaagtgat ctccaggtct    15000
ttgtatgcca ctgaggtaac cgttccctcc accccccaga cctcccaaaa gcaacttggc    15060
aactggcagc tcttctgctg tggccctcc agtgagctca ccaaaagcag ccctggtttt    15120
cagagtccca cctagtcaac acccttcccc ctttcgatgg ggctgctctt acccagtgac    15180
tttgctgcca ggaacgagtc ctgcaagtgc tttcctcagc tcaagggcag aatggggtat    15240
ggccgggcct cctatgtatg atggcctttc tctgagtgac tgacagctgt gtccctatag    15300
gcagtggtca ctcatgcagg cagtaactgg ccacagggca ggtgaccagg ggaggaagga    15360
gacagaccca ccaaggagag ctggggccag ctgtccccc tccaccactg ctgccaccag    15420
aacgcagcta ccaatgggcc agggtctggc catggggtca gggacatttt cctcctgcag    15480
gtggatatct ggtctctggg catcatggtg attgagatgg tagatgggga gccaccgtac    15540
ttcagtgact ccccagtgca agccatgaag aggctccggg acagccccc acccaagctg    15600 aaaaactctc acaaggtcag ttggcacaca agggtgcgac ctcgcagacc ccattcctcc    15660
tgaggcaagg ggaccagaac ctgggctccc agcatctccc ttccactgaa gccacagggt    15720
ctgggctcct ggaaaaggct cctctttccc cacacaaaac ccgcacctgg gtgtggagcc    15780
gcatctacgc acaagttcgc atgtgcgctc cgacaagtcg cctcccacgg ctgtggcagg    15840
agagttgctg cttggcagaa gggttgctgc ttggcaggca ctggtcggaa gcccagtggg    15900
gcccatgagc agggaaagcc aggacaccag caatccctgc tgtccaggga gggatccgga    15960
gaagcttcac tgagcacaaa cccttctaac ccgtgtcggg agatccatac catgattcga    16020
tgtccctgtc catcacggcg agtcggctca tgctccatcg ttgcacaccc cgacacagct    16080
aagccacagc gttcccctta aagccagtat aagtgcatgg aagtgtatac atgtaaccct    16140
ttttgccaaa tcggcccaa ccccgcaggc cttactgtgg acgcccctg ctggcaggtc    16200 agcacggggc tgctaagtgg caccgccatc tggtggccaa acaagaaat gtctcagagg    16260
```

```
gctgaagcct ctcctctaaa atagcaaaaa aacaagagtt ctgtggcccc aacacaaagc    16320
tggatgggag gaccaacagg aaacatcttc caagacaact ggtccttgga gcccgcaccg    16380
ctaaccccaa aattagcata taaagatctc cagttggcta attcctcaga ggatgtagcc    16440
ttctgcccaa gactcagcct catcccaaga tactggctca aaatgaacca agataagccc    16500
ttgctttaga ctcttaaggc ctagagcaac aaagaaatct tccttttcag gtctcacttt    16560
attttctatt tttcagagta cttcctcatc cttgacttgt ttgtttctgt tgttgttggt    16620
tttttttttt tttttttttt tggagatgga gtctctctct gttgctcagg ctggaatgca    16680
gtggtgcgat ctcagctcac tgcaacctcc gcctcctggg ttcaagcaat tctcctgcct    16740
cagcctcctg agtagctggg attacaggca cgtgccacca tgctcaacta attttgtat     16800 ttttagtaga gacagggttt cgccatgttg gtcaggctgg tctacgaact cctgacctcg    16860
taatctgccc aacttggcct cccaaagtgc tgggattaca ggcttgagcc actgcgccca    16920
gcgacctgtt tttaaaatct caaaagccct atgtggcaga cagggcaagc atactttatc    16980
actagcccat tttacagatg agaaaactga ggcctagaga aaactgtgac ttgcctgaga    17040
tcacggatag agccagatct ggatcactga tgccaatcct ctgccccttc cacagagcta    17100
tagcatctga atgctgagag ccttgagggg gtggggaggg acaagggaac aggaagttaa    17160
aaaaccagcg aattcatgac tttcaaacaa tgataagtcc aggcaatcag gtcaccccga    17220
agtgactgca aattgtggct tcatcttact gccctgcctc tacaggtctc cccagtgctg    17280
cgagacttcc tggagcggat gctggtgcgg gaccccaag agagccac agcccaggag       17340 ctcctagacc accccttcct gctgcagaca gggctacctg agtgcctggt gccctgatc     17400 cagctctacc gaaagcagac ctccacctgc tgagcccacc ccaagtatgc ctgccaccta    17460
cgcccacagg cagggcacac tgggcagcca gcctgccggc aggacttgcc tgcctcctcc    17520
tctcagtatt ctctccaaag attgaaatgt gaagcccag cccaccctc tgcccttcag      17580 cctactgggc caggccggac ctgcccctc agtgtctctc cctcccgagt ccccagatgg     17640 agacccttt ctacaggatg acccctgat atttgcacag ggatatttct aagaaacgca      17700
gaggccagcg ttcctggcct ctgcagccaa cacagtagaa aaggctgctg tggttttta    17760 aaggcagttg tccactagtg tcctaggcca ctgcagaggg cagactgctg gtctccacag    17820
atacctgctg ttctcagctc cagcttcaaa cctcgagtct cgagagggcc acgggtggt     17880 tttatgacc ggaatcccgc ttcctccctc acgtctgatg tcctgaaggt gcagtcccac     17940
ctgtacagcc cctccccgcc cagaactgtg aatggcctgc tccaggccat ggctggggc     18000 agggagtgag gggacaattt ctgagtgaaa gagaaagaat ggggtcggtg gtgaaggtgc    18060
tctcacttta cagaatggag agaacatcgt gtgtgtgtgt gtgtgtgtgt gtgtgtgtgt    18120
gtgtgtgtaa ggggaggaaa gccaccttga cagcccaggt ccctccaggt cacccacagc    18180
cagtttcagg aaggctgccc ctctctccca ctaagtctg gcctgaaggg acctgctttc     18240
ttggcctggc ttccacctct ccactcctgt gtctacctgg ccagtggagt ggtccatgct    18300
aagtctaaca ctcctgggag ctcaggaggc ttctgagctt ctcctgtact gtgcatcgtg    18360
agggccagag acaggaatgt aaggattggc aactgtgtta cctttcaagt ttatctcaat    18420
aaccaggtca tcaggaccc attgttctct tcagaaccct atctgggaga gaaggcgaac     18480
cacctccggg tttccatcat gtcaaggtca caggcatcca tgtgtgcaaa ccatctgccc    18540
cagctgcctc cacagactgc tgtctccttg tcctcctcgg ccctgcccca cttcagggct    18600
gctgtgagat ggaattccag gaaagaactt caggtgtctg gaccctttct atctagataa    18660
```

-continued

```
tatttttaga ttcttctgct ccctagtgac ctacctgggg gcaaagaaat tgcaaggact    18720 ttttttttaag ggtcagagtt ttcaaaacaa aagcatcttc cctagaaatt tttgtgaatt    18780
gtttgcactt gtgcctgttt taaattaaat tgagtgttca aagccattgg gcttcctgtg    18840
tctctgggag cggagaccgg ccgtcttgga gggggtctc ctgtggcggg tgaatctcgt    18900
gtagcctccc ctcctcccca cgtgagctct ccagcagcca caccacagaa cacccaactt    18960
ccctggtggc ctgtggaccc gaaaggaggg cagagaggaa gggaaacagg aagtgaaagg    19020
cccttgggaa tgaaggcg                                                  19038
```

<210> SEQ ID NO 12
<211> LENGTH: 146
<212> TYPE: DNA
<213> ORGANISM: Homo sapiens
<220> FEATURE:
<221> NAME/KEY: CDS
<222> LOCATION: (2)...(145)

<400> SEQUENCE: 12

```
g cac cgg gat atc aag ggg cag aat gtg ctg ctg aca gag aat gct gag      49
  His Arg Asp Ile Lys Gly Gln Asn Val Leu Leu Thr Glu Asn Ala Glu
    1               5                  10                  15 gtc aag cta gtg gat ttt ggg gtg agt gct cag gtg gac cgc acc gtg        97
Val Lys Leu Val Asp Phe Gly Val Ser Ala Gln Val Asp Arg Thr Val
             20                  25                  30 ggc aga cgg aac act ttc att ggg act ccc tac tgg atg gcc ccc gag       145
Gly Arg Arg Asn Thr Phe Ile Gly Thr Pro Tyr Trp Met Ala Pro Glu
         35                  40                  45 g                                                                     146
```

<210> SEQ ID NO 13
<211> LENGTH: 48
<212> TYPE: PRT
<213> ORGANISM: Homo sapiens

<400> SEQUENCE: 13

```
His Arg Asp Ile Lys Gly Gln Asn Val Leu Leu Thr Glu Asn Ala Glu
  1               5                  10                  15

Val Lys Leu Val Asp Phe Gly Val Ser Ala Gln Val Asp Arg Thr Val
             20                  25                  30

Gly Arg Arg Asn Thr Phe Ile Gly Thr Pro Tyr Trp Met Ala Pro Glu
         35                  40                  45
```

<210> SEQ ID NO 14
<211> LENGTH: 18
<212> TYPE: DNA
<213> ORGANISM: Homo sapiens
<220> FEATURE:
<221> NAME/KEY: misc_feature
<222> LOCATION: 9
<223> OTHER INFORMATION: n = A,T,C or G

<400> SEQUENCE: 14

```
atgcamcang ayathaar                                                    18
```

<210> SEQ ID NO 15
<211> LENGTH: 20
<212> TYPE: DNA
<213> ORGANISM: Homo sapiens
<220> FEATURE:
<221> NAME/KEY: misc_feature
<222> LOCATION: 3, 9, 12

```
<223> OTHER INFORMATION: n = A,T,C or G

<400> SEQUENCE: 15
gcnacytcng gngccatcca                                              20

<210> SEQ ID NO 16
<211> LENGTH: 27
<212> TYPE: DNA
<213> ORGANISM: Homo sapiens
<220> FEATURE:
<221> NAME/KEY: misc_feature
<222> LOCATION: 18
<223> OTHER INFORMATION: n = A,T,C or G

<400> SEQUENCE: 16
cccgaattca tgcamcanga yathaar                                      27

<210> SEQ ID NO 17
<211> LENGTH: 29
<212> TYPE: DNA
<213> ORGANISM: Homo sapiens
<220> FEATURE:
<221> NAME/KEY: misc_feature
<222> LOCATION: 12, 18, 21
<223> OTHER INFORMATION: n = A,T,C or G

<400> SEQUENCE: 17
cccgaattcg cnacytcngg ngccatcca                                    29

<210> SEQ ID NO 18
<211> LENGTH: 17
<212> TYPE: DNA
<213> ORGANISM: Homo sapiens

<400> SEQUENCE: 18
gagtgactcc atcctgc                                                 17

<210> SEQ ID NO 19
<211> LENGTH: 17
<212> TYPE: DNA
<213> ORGANISM: Homo sapiens

<400> SEQUENCE: 19
gtagggggtt cccacca                                                 17
```